(12) United States Patent
Ercolani et al.

(10) Patent No.: US 7,662,809 B2
(45) Date of Patent: Feb. 16, 2010

(54) TETRACYCLIC INDOLE DERIVATIVES AS ANTIVIRAL AGENTS

(75) Inventors: Caterina Ercolani, Rome (IT); Joerg Habermann, Pomezia (IT); Frank Narjes, Ariccia (IT); Simona Ponzi, Rome (IT); Michael Rowley, Axa (IT); Ian Stansfield, Ariccia (IT)

(73) Assignee: Istituto di Richerche di Biologia Molecolare P Angeletti SpA, Pomezia, Rome (IT)

( * ) Notice: Subject to any disclaimer, the term of this patent is extended or adjusted under 35 U.S.C. 154(b) by 0 days.

(21) Appl. No.: 11/666,583

(22) PCT Filed: Oct. 25, 2005

(86) PCT No.: PCT/GB2005/004144

§ 371 (c)(1),
(2), (4) Date: Jan. 24, 2008

(87) PCT Pub. No.: WO2006/046039

PCT Pub. Date: May 4, 2006

(65) Prior Publication Data

US 2008/0261938 A1    Oct. 23, 2008

(30) Foreign Application Priority Data

Oct. 26, 2004 (GB) ................... 0423767.3
Jun. 21, 2005 (GB) ................... 0512519.0

(51) Int. Cl.
 *C07D 223/18* (2006.01)
 *A61K 31/407* (2006.01)
(52) U.S. Cl. ............... 514/183; 514/214.01; 514/215; 540/461; 540/476; 540/576
(58) Field of Classification Search ............ 514/183, 514/214.01, 215; 540/461, 476, 576
See application file for complete search history.

(56) References Cited

U.S. PATENT DOCUMENTS 5,206,382 A    4/1993   Costa et al.
7,153,848 B2 * 12/2006  Hudyma et al. ......... 514/214.01
2006/0100262 A1  5/2006  Conte et al.

FOREIGN PATENT DOCUMENTS

| EP | 1 719 773 A1 | 11/2006 |
| WO | WO 93/00334 A1 | 1/1993 |
| WO | WO 96/37619 A1 | 11/1996 |
| WO | WO 02/059321 A2 | 8/2002 |
| WO | WO 2004/087714 A1 | 10/2004 |
| WO | WO 2005/080399 A1 | 9/2005 |
| WO | WO 2006/046030 A2 | 5/2006 |
| WO | WO 03/099824 A1 | 12/2006 |

OTHER PUBLICATIONS

V. Lohmann et al., Replication of Subgenomic Hepatitis C Virus RNAs in a Hepatoma Cell Line, Science, vol. 285, 110-113 (1999).
W. Clark Still et al., Rapid Chromatographic Technique for Preparative Separations with Moderate Resolution, Journal of Organic Chemistry, 43(14) 2923-2925 (1978).
Michael J. Szmynifka & James V. Heck, The Synthesis and Reactions of 4-Carbomethoxy B-Sultams, Tetrahedron Letters, 30(22) 2869-2872 (1989).

* cited by examiner

*Primary Examiner*—Bruck Kifle
(74) *Attorney, Agent, or Firm*—Julie M. Lake; Sheldon O. Heber

(57) ABSTRACT

The present invention relates to tetracyclic indole compounds of formula (I); wherein $R^1$, $R^2$, $R^{14}$, $R^{15}$, A, Ar, Y and Z are defined herein, and pharmaceutically acceptable salts thereof, pharmaceutical compositions comprising them, and their use for the treatment or prevention of infection by hepatitis C virus.

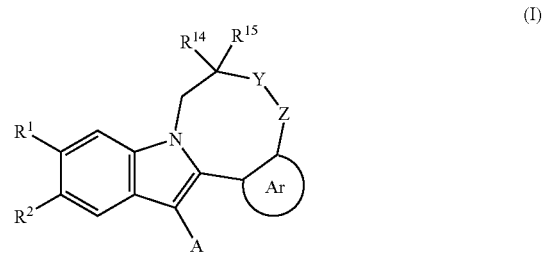

(I)

10 Claims, No Drawings

TETRACYCLIC INDOLE DERIVATIVES AS ANTIVIRAL AGENTS

CROSS-REFERENCE TO RELATED APPLICATIONS

This application is a U.S. National Phase application under 35 U.S.C. 371 of International Application No. PCT/GB2005/004144, filed Oct. 25, 2005, which claims priority to United Kingdom Patent Application No. 0423767.3, filed Oct. 26, 2004, and United Kingdom Patent Application No. 0512518.0, filed Jun. 21, 2005.

The present invention relates to tetracyclic indole compounds, to pharmaceutical compositions containing them, to their use in the prevention and treatment of hepatitis C infections and to methods of preparation of such compounds and compositions.

Hepatitis C (HCV) is a cause of viral infections. There is as yet no adequate treatment for HCV infection but it is believed that inhibition of its RNA polymerase in mammals, particularly humans, would be of benefit.

Published International patent application WO 93/00334 (Fidia-Georgetown Institute for the Neurosciences) discloses the following indole derivatives:

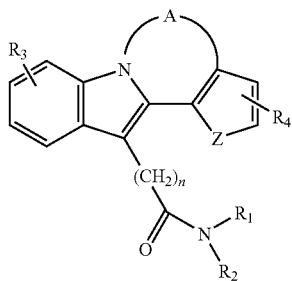

where A, Z, $R_1$, $R_2$, $R_3$, $R_4$ and n are defined therein, as useful in compositions and methods for treating psychiatric and neurological disorders. However, this document does not disclose the use of tetracyclic indole derivatives in treating or preventing viral infections.

Published International patent application WO 2005/080399 (Japan Tobacco Inc.) discloses the following fused heterotetracyclic compounds:

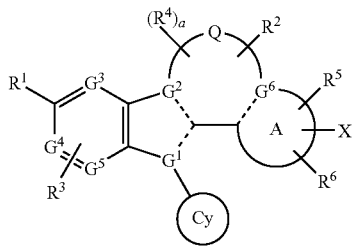

where A, X, Cy, $G^1$, $G^2$, $G^3$, $G^4$, $G^5$, $G^6$, $R^1$, $R^2$, $R^3$, $R^4$, $R^5$, $R^6$ and a are defined therein, and their use as HCV polymerase inhibitors.

The present invention provides the compound of the formula (I):

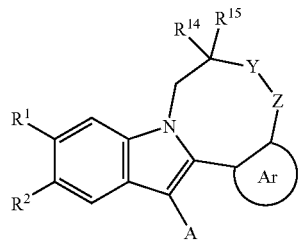

wherein

A is $C_{3-8}$cycloalkyl, optionally substituted by halogen, hydroxy, $C_{1-4}$alkyl or $C_{1-4}$alkoxy;

Ar is a moiety containing at least one aromatic ring and possesses 5, 6, 9 or 10 ring atoms, optionally containing 1, 2 or 3 heteroatoms independently selected from N, O and S, such as phenyl, pyridyl, pyridazinyl, pyrimidinyl, pyrazinyl, thienyl, furanyl, pyrazolyl and imidazolyl, which ring is optionally substituted by groups $Q^1$ and $Q^2$;

$Q^1$ is halogen, hydroxy, $C_{1-6}$alkyl, $C_{1-6}$alkoxy, $(CH_2)_{0-3}$aryl, heteroaryl, $CONR^cR^d$, $(CH_2)_{0-3}NR^cR^d$, $O(CH_2)_{0-3}C_{3-8}$cycloalkyl, $O(CH_2)_{1-3}NR^cR^d$, $O(CH_2)_{0-3}CONR^cR^d$, $O(CH_2)_{0-3}CO_2H$, $O(CH_2)_{0-3}$aryl, $O(CH_2)_{0-3}$heteroaryl, $OCHR^eR^f$ or $O(CH_2)_{0-3}S(O)_2(CH_2)_{0-3}NR^cR^d$;

$R^c$ and $R^d$ are independently selected from hydrogen, $C_{1-6}$alkyl and $C(O)C_{1-6}$alkyl;

or $R^c$ and $R^d$, together with the nitrogen atom to which they are attached, form a heteroaliphatic ring of 4 to 7 ring atoms, optionally containing 1 or 2 more heteroatoms independently selected from O and S and/or 1 or 2 groups independently selected from NH and $NC_{1-4}$alkyl, where said ring is optionally substituted by halogen, hydroxy, $C_{1-4}$alkyl or $C_{1-4}$alkoxy;

$R^e$ and $R^f$ are independently selected from hydrogen, $C_{1-4}$alkyl and $C_{1-4}$alkoxy;

or $R^e$ and $R^f$ are linked by a heteroatom selected from N, O and S to form a heteroaliphatic ring of 4 to 7 ring atoms, where said ring is optionally substituted by halogen, hydroxy, $C_{1-4}$alkyl or $C_{1-4}$alkoxy;

and where said $C_{1-4}$alkyl, $C_{1-4}$alkoxy and aryl groups are optionally substituted by halogen or hydroxy;

$Q^2$ is halogen, hydroxy, $C_{1-4}$alkyl or $C_{1-4}$alkoxy, where said $C_{1-4}$alkyl and $C_{1-4}$alkoxy groups are optionally substituted by halogen or hydroxy;

or $Q^1$ and $Q^2$ may be linked to form a ring of 4 to 7 atoms, where said ring optionally contains 1 or 2 heteroatoms independently selected from N, O and S, and is optionally substituted by halogen, hydroxy, $C_{1-4}$alkyl or $C_{1-4}$alkoxy;

one of $R^1$ and $R^2$ is $CO_2H$, $C(O)NHS(O)_2NR^aR^b$, $C(O)NHS(O)_2C_{1-6}$alkyl, $C(O)NHS(O)_2(CH_2)_{0-3}CO_2R^c$ or $C(O)NHS(O)_2(CH_2)_{0-3}$aryl, and the other of $R^1$ and $R^2$ is hydrogen;

$R^a$ and $R^b$ are independently selected from hydrogen and $C_{1-6}$alkyl, or $R^a$ and $R^b$, together with the nitrogen atom to which they are attached, form a heteroaliphatic ring of 4 to 7 ring atoms, which ring may optionally contain 1 or 2 more heteroatoms independently selected from O and S and/or 1 or 2 groups independently selected from $S(O)$, $S(O)_2$, NH and $NC_{1-4}$alkyl;

Y is C=O or —$CR^{14a}R^{15a}$;

Z is a bond or $NR^{10}$;

$R^{10}$ is hydrogen, hydroxy, $C_{1-6}$alkyl, $C_{2-6}$alkenyl, $C_{2-6}$alkynyl, $C_{1-6}$alkoxy, $C(O)C_{1-6}$alkyl, Het, $(CH_2)_{0-3}NR^{16}R^{17}$, $C(O)(CH_2)_{0-3}NR^{16}R^{17}$ and $NHC(O)(CH_2)_{0-3}NR^{16}R^{17}$;

$R^{14}$, $R^{14a}$, $R^{15a}$ and $R^{15a}$ are each independently selected from hydrogen, hydroxy, $C_{1-6}$alkyl, $C_{2-6}$alkenyl, $C_{2-6}$alkynyl, $(CH_2)_{0-3}C_{3-8}$cycloalkyl, $C_{1-6}$alkoxy, $C(O)C_{1-6}$alkyl, $(CH_2)_{0-3}$aryl, $(CH_2)_{0-3}$Het, $C(O)(CH_2)_{0-3}$Het, $(CH_2)_{0-3}NR^{16}R^{17}$, $(CH_2)_{0-3}OR^{16}$, $(CH_2)_{0-3}C(O)(CH_2)_{0-3}NR^{16}R^{17}$, $NR^{18}C(O)(CH_2)_{0-3}NR^{16}R^{17}$, $S(O)_{0-2}(CH_2)_{0-3}NR^{16}R^{17}$, $(CH_2)_{0-3}$heteroaryl or $C(O)(CH_2)_{0-3}$heteroaryl, optionally substituted by one or two groups independently selected from $C_{1-6}$alkyl, hydroxy, halogen, $C_{1-6}$alkoxy, SH and $S(C_{1-6}$alkyl);

$R^{16}$ and $R^{17}$ are independently selected from hydrogen, $C_{1-6}$alkyl, $(CH_2)_{0-4}NR^{18}R^{,19}$ $(CH_2)_{0-3}$Het, $(CH_2)_{0-3}$heteroaryl, $(CH_2)_{0-3}C(O)(CH_2)_{0-3}NR^{18}R^{19}$ or $(CH_2)_{0-3}C_{3-8}$cycloalkyl, optionally substituted by $C_{1-6}$alkyl, $(CH_2)_{0-3}$OH or $(CH_2)_{0-3}C_{1-6}$alkoxy;

or $R^{16}$ and $R^{17}$, together with the nitrogen atom to which they are attached, form a heteroaliphatic ring of 4 to 7 ring atoms, which ring may optionally contain 1 or 2 more heteroatoms selected from O and S and/or 1 or 2 groups independently selected from S(O), $S(O)_2$, NH, $NC_{1-4}$alkyl and $N(CH_2)_{0-3}C_{1-4}$alkoxy, and which ring is optionally substituted by halogen, hydroxy, $C_{1-4}$alkyl or $C_{1-4}$alkoxy;

$R^{18}$ and $R^{19}$ are independently selected from hydrogen, $C_{1-6}$alkyl and heteroaryl;

or $R^{18}$ and $R^{19}$, together with the nitrogen atom to which they are attached, form a heteroaliphatic ring of 4 to 7 ring atoms, which ring may optionally contain 1 or 2 more heteroatoms selected from O and S and/or 1 or 2 groups selected from S(O), $S(O)_2$, NH and $NC_{1-4}$alkyl, and which ring is optionally substituted by halogen, hydroxy, $C_{1-4}$alkyl or $C_{1-4}$alkoxy;

and pharmaceutically acceptable salts thereof;

with the proviso that the compound of formula (I) is not methyl 13-cyclohexyl-6,7-dihydro-5H-indolo[2,1-a][2]benzazepine-10-carboxylate, or 13-cyclohexyl-6,7-dihydro-5H-indolo[2,1-a][2]benzazepine-10-carboxylic acid.

Another favoured group of compounds of the present invention is the compound of formula (Ia):

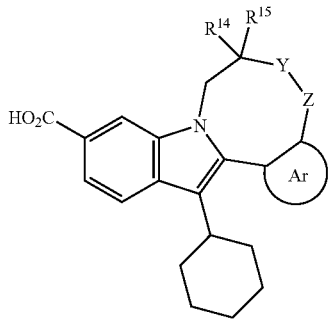

(Ia)

wherein

Ar is a five- or six-membered aromatic ring optionally containing 1, 2 or 3 heteroatoms independently selected from N, O, and S;

Y is C=O or —$CR^{14a}R^{15a}$—;

Z is a bond or $NR^{10}$;

$R^{10}$, $R^{14}$, $R^{15}$, $R^{14a}$ and $R^{15a}$ are each independently selected from hydrogen, hydroxy, $C_{1-6}$alkyl, $C_{2-6}$alkenyl, $C_{1-6}$alkoxy, $C(O)C_{1-6}$alkyl, Het, $(CH_2)_{0-3}NR^{16}R^{17}$, $C(O)(CH_2)_{0-3}NR^{16}R^{17}$ and $NHC(O)(CH_2)_{0-3}NR^{16}R^{17}$;

$R^{16}$ and $R^{17}$ are independently selected from hydrogen, $C_{1-6}$alkyl and $(CH_2)_{0-4}NR^{18}R^{19}$;

or $R^{16}$, $R^{17}$ and the nitrogen atom to which they are attached form a heteroaliphatic ring of 4 to 7 ring atoms, which ring may optionally contain 1 or 2 more heteroatoms selected from O or S or a group S(O), $S(O)_2$, NH or $NC_{1-4}$alkyl, and which ring is optionally substituted by halogen, hydroxy, $C_{1-4}$alkyl or $C_{1-4}$alkoxy;

$R^{18}$ and $R^{19}$ are independently selected from hydrogen and $C_{1-6}$alkyl;

or $R^{18}$, $R^{19}$ and the nitrogen atom to which they are attached form a heteroaliphatic ring of 4 to 7 ring atoms, which ring may optionally contain 1 or 2 more heteroatoms selected from O or S or a group S(O), $S(O)_2$, NH or $NC_{1-4}$alkyl, and which ring is optionally substituted by halogen, hydroxy, $C_{1-4}$alkyl or $C_{1-4}$alkoxy;

and pharmaceutically acceptable salts thereof;

with the proviso that the compound of formula (Ia) is not methyl 13-cyclohexyl-6,7-dihydro-5H-indolo[2,1-a][2]benzazepine-10-carboxylate.

In one embodiment, Ar is a five- or six-membered aromatic ring optionally containing 1 or 2 heteroatoms independently selected from N, O and S. Preferably, Ar is a five- or six-membered aromatic ring optionally containing one heteroatom selected from N, O and S. More preferably, Ar is phenyl, pyridinyl, furyl or thienyl. Most preferably, Ar is phenyl or thienyl.

When Z is $NR^{10}$, preferably $R^{10}$ is hydrogen, $C_{1-6}$alkyl or $(CH_2)_{0-3}NR^{16}R^{17}$, where $R^{16}$ and $R^{17}$ are as defined in relation to formula (Ia). More preferably, $R^{10}$ is $C_{1-6}$alkyl or $(CH_2)_{1-3}NR^{16}R^{17}$, where $R^{16}$ and $R^{17}$ are independently selected from hydrogen and $C_{1-6}$alkyl. Most preferably, $R^{10}$ is $C_{1-4}$alkyl or $(CH_2)_{1-3}NR^{16}R^{17}$, where $R^{16}$ and $R^{17}$ are independently selected from hydrogen and $C_{1-4}$alkyl. Examples of suitable $R^{10}$ groups include methyl and $(CH_2)_2N(CH_3)_2$.

In another embodiment, $R^{14}$, $R^{15}$, $R^{14a}$ and $R^{15a}$ are each independently selected from hydrogen, $C_{1-6}$alkyl and $(CH_2)_{0-3}NR^{16}R^{17}$, where $R^{16}$ and $R^{17}$ are as defined in relation to formula (Ia). Preferably $R^{14}$, $R^{15}$, $R^{14a}$ and $R^{15a}$ are each independently selected from hydrogen and $(CH_2)_{0-3}NR^{16}R^{17}$, where $R^{16}$ and $R^{17}$ are independently selected from hydrogen, $C_{1-4}$alkyl and $(CH_2)_{1-3}NR^{18}R^{19}$, where $R^{18}$ and $R^{19}$ are as defined in relation to formula (Ia). More preferably, $R^{14}$, $R^{15}$, $R^{14a}$ and $R^{15a}$ are each independently selected from hydrogen and $NR^{16}R^{17}$ where $R^{16}$ and $R^{17}$ are independently selected from hydrogen, methyl and $(CH_2)_{1-3}$ $NR^{18}R^{19}$, where $R^{18}$ and $R^{19}$ are independently selected from hydrogen and $C_{1-4}$alkyl. Examples of suitable $R^{14}$, $R^{15}$, $R^{14a}$ and $R^{15a}$ groups include hydrogen, $NH(CH_2)_2N(CH_3)_2$ and $N(CH_3)(CH_2)_2N(CH_3)_2$.

In another embodiment, Y is —$CR^{14a}R^{15a}$—. Preferably, Y is —$CHR^{14a}$—.

Another favoured group of compounds of the present invention is of formula (Ib) and pharmaceutically acceptable salts thereof:

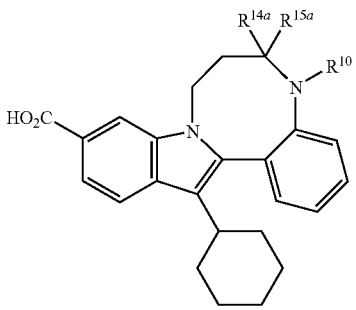

(Ib)

wherein
$R^{10}$ is hydrogen, $C_{1-6}$alkyl, $C_{2-6}$alkenyl, $C_{2-6}$alkynyl or $(CH_2)_{1-3}NR^{16}R^{17}$;
$R^{16}$ and $R^{17}$ are independently selected from hydrogen and $C_{1-6}$alkyl;
$R^{14a}$ and $R^{15a}$ are independently selected from hydrogen, $C_{1-6}$alkyl, $C_{2-6}$alkenyl, $C_{2-6}$alkynyl or $C_{3-8}$cycloalkyl;
or $R^{14a}$ and $R^{15a}$ together form an oxo group;
with the proviso that the compound of formula (Ib) is not 3-chloro-14-cyclohexyl-5-(2-piperidin-1-ylethyl)-5,6,7,8-tetrahydroindolo[1,2-e][1,5]benzodiazocine-11-carboxylic acid.

In one embodiment, $R^{10}$ is hydrogen, $C_{1-6}$alkyl or $(CH_2)_{1-3}NR^{16}R^{17}$, where $R^{16}$ and $R^{17}$ are as defined in relation to formula (Ib). Preferably, $R^{10}$ is $C_{1-6}$alkyl or $(CH_2)_{1-3}NR^{16}R^{17}$, where $R^{16}$ and $R^{17}$ are independently selected from hydrogen and $C_{1-4}$alkyl. More preferably, $R^{10}$ is $C_{1-4}$alkyl or $(CH_2)_2N(C_{1-4}alkyl)_2$. Examples of suitable $R^{10}$ groups include methyl and $(CH_2)N(CH_3)_2$.

In another embodiment, $R^{14a}$ and $R^{15a}$ are independently selected from hydrogen or $C_{1-6}$alkyl, or $R^{14a}$ and $R^{15a}$ together form an oxo group. Preferably, $R^{14a}$ and $R^{15a}$ are independently selected from hydrogen or $C_{1-4}$alkyl, or $R^{14a}$ and $R^{15a}$ together form an oxo group. More preferably, $R^{14a}$ and $R^{15a}$ are both hydrogen, or $R^{14a}$ and $R^{15a}$ together form an oxo group.

Another favoured group of compounds of the present invention is of formula (Ic) and pharmaceutically acceptable salts thereof:

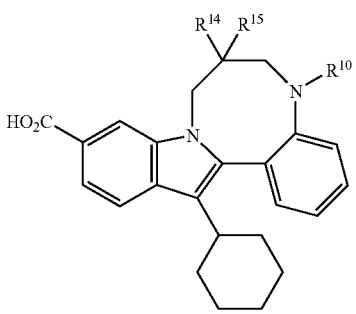

(Ic)

wherein
$R^{10}$ is hydrogen, $C_{1-6}$alkyl, $C_{2-6}$alkenyl or $C_{2-6}$alkynyl;
$R^{14}$ and $R^{15}$ are independently selected from hydrogen, $C_{1-6}$alkyl, $C_{2-6}$alkenyl, $C_{2-6}$alkynyl or $(CH_2)_{0-3}NR^{16}R^{17}$; and $R^{16}$ and $R^{17}$ are independently selected from hydrogen and $C_{1-6}$alkyl.

In one embodiment, $R^{10}$ is hydrogen or $C_{1-6}$alkyl. Preferably, $R^{10}$ is hydrogen or $C_{1-4}$alkyl. More preferably, $R^{10}$ is methyl.

In another embodiment, $R^{14}$ and $R^{15}$ are independently selected from hydrogen, $C_{1-6}$alkyl or $(CH_2)_{0-3}NR^{16}R^{17}$, where $R^{16}$ and $R^{17}$ are independently selected from hydrogen and $C_{1-4}$alkyl. Preferably, $R^{14}$ and $R^{15}$ are independently selected from hydrogen, $C_{1-4}$alkyl or $NR^{16}R^{17}$, where $R^{16}$ and $R^{17}$ are independently selected from hydrogen and methyl. More preferably, $R^{14}$ and $R^{15}$ are hydrogen or $N(CH_3)_2$.

Another favoured group of compounds of the present invention is of formula (Id) and pharmaceutically acceptable salts thereof:

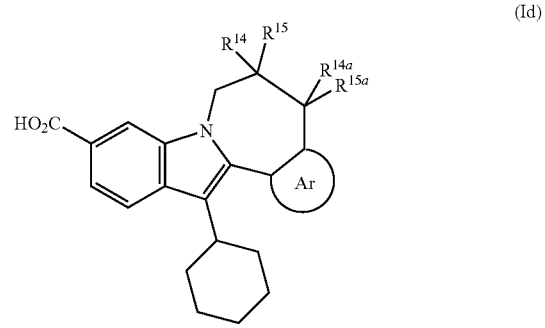

(Id)

wherein
Ar is a five- or six-membered aromatic ring optionally containing 1, 2 or 3 heteroatoms independently selected from N, O and S, which ring is optionally substituted by group $Q^1$;
$R^{14}$, $R^{15}$, $R^{14a}$, $R^{15a}$ and $Q^1$ are as defined in relation to formula (I), with the proviso that the compound of formula (Id) is not
methyl 13-cyclohexyl-6,7-dihydro-5H-indolo[2,1-a][2]benzazepine-10-carboxylate, or
13-cyclohexyl-6,7-dihydro-5H-pyrrolo[2',1':3,4][1,4]diazepino[1,2-a]indole-10-carboxylic acid.

In one embodiment, Ar is a five- or six-membered aromatic ring optionally containing 1 or 2 heteroatoms independently selected from N, O and S, which ring is optionally substituted by halogen, hydroxy, $C_{1-6}$alkyl or $C_{1-6}$alkoxy. Preferably, Ar is a five- or six-membered aromatic ring optionally containing one heteroatom selected from N, O and S, which ring is optionally substituted by halogen, hydroxy or $C_{1-4}$alkoxy. More preferably, Ar is a five- or six-membered aromatic ring optionally containing one S atom, which ring is optionally substituted by $C_{1-4}$alkoxy. More preferably, Ar is phenyl or thienyl, optionally substituted by methoxy.

In another embodiment, $R^{14}$, $R^{15}$, $R^{14a}$ and $R^{15a}$ are independently selected from hydrogen, $C_{1-6}$alkyl, $(CH_2)_{0-3}OR^{16}$ and $(CH_2)_{0-3}NR^{16}R^{17}$, where $R^{16}$ and $R^{17}$ are as defined in relation to formula (Id). Preferably, one of $R^{14}$ and $R^{14a}$ is hydrogen, $C_{1-6}$alkyl, $(CH_2)_{0-3}OR^{16}$ or $(CH_2)_{0-3}NR^{16}R^{17}$, where $R^{16}$ and $R^{17}$ are as defined in relation to formula (I), and the other of $R^{14}$ and $R^{14a}$ is hydrogen. More preferably, one of $R^{14}$ and $R^{14a}$ is $(CH_2)_{0-3}OR^{16}$ or $(CH_2)_{0-3}NR^{16}R^{17}$, where $R^{16}$ and $R^{17}$ are as defined in relation to formula (Id), and the other of $R^{14}$ and $R^{14a}$ is hydrogen. Most preferably, one of $R^{14}$ and $R^{14a}$ is $OR^{16}$ or $NR^{16}R^{17}$, where $R^{16}$ and $R^{17}$ are as defined in relation to formula (I), and the other of $R^{14}$ and $R^{14a}$ is hydrogen.

When any one or more of $R^{14}$, $R^{15}$, $R^{14a}$ and $R^{15a}$ is $(CH_2)_{0-3}OR^{16}$ or $(CH_2)_{1-3}NR^{16}R^{17}$, preferably $R^{16}$ and $R^{17}$ are independently selected from hydrogen, $C_{1-6}$alkyl, $(CH_2)_{0-4}NR^{18}R^{19}$, $(CH_2)_{0-3}$Het, $(CH_2)_{0-3}$heteroaryl, $(CH_2)_{0-3}C(O)(CH_2)_{0-3}NR^{18}R^{19}$ or $(CH_2)_{0-3}C_{3-8}$cycloalkyl, where $R^{18}$ and $R^{19}$ are as defined in relation to formula (I). More preferably, $R^{16}$ and $R^{17}$ are independently selected from hydrogen, $C_{1-6}$alkyl and $(CH_2)_{1-3}NR^{18}R^{19}$, where $R^{18}$ and $R^{19}$ are as defined in relation to formula (I). Most preferably, $R^{16}$ and $R^{17}$ are independently selected from hydrogen, $C_{1-4}$alkyl and $(CH_2)_{1-3}NR^{18}R^{19}$, where $R^{18}$ and $R^{19}$ are independently selected from hydrogen and $C_{1-6}$alkyl, or $R^{18}$ and $R^{19}$ together with the nitrogen atom to which they are attached, form a heteroaliphatic ring of 5 or 6 ring atoms, which ring may optionally contain 1 more O or S atom and/or a NH or $NC_{1-4}$alkyl group. Especially, $R^{16}$ and $R^{17}$ are independently selected from hydrogen, methyl and $(CH_2)_2NR^{18}R^{19}$, where $R^{18}$ and $R^{19}$ are independently selected from methyl and ethyl, or $R^{18}$ and $R^{19}$, together with the nitrogen atom to which they are attached form a pyrrolidinyl ring. Examples of suitable $R^{14}$, $R^{15}$, $R^{14a}$ and $R^{15a}$ groups include hydrogen,

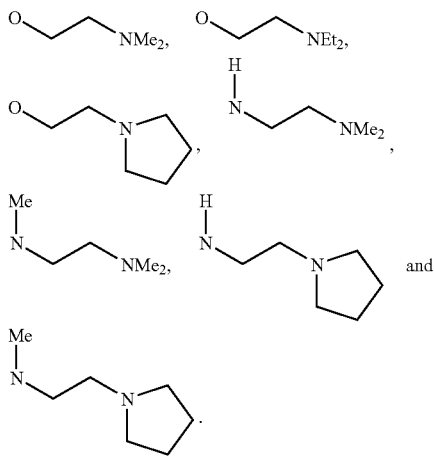

Preferably, $R^{15}$ and $R^{15a}$ are independently selected from hydrogen and $C_{1-6}$alkyl. More preferably, $R^{15}$ and $R^{15a}$ are independently selected from hydrogen and $C_{1-4}$alkyl. Most preferably, $R^{15}$ and $R^{15a}$ are independently selected from hydrogen, methyl and ethyl. Especially, $R^{15}$ and $R^{15a}$ are both hydrogen.

When any variable occurs more than one time in formula (I) or in any substituent, its definition on each occurrence is independent of its definition at every other occurrence.

As used herein, the term "alkyl" or "alkoxy" as a group or part of a group means that the group is straight or branched. Examples of suitable alkyl groups include methyl, ethyl, n-propyl, i-propyl, n-butyl, s-butyl and t-butyl. Examples of suitable alkoxy groups include methoxy, ethoxy, n-propoxy, i-propoxy, n-butoxy, s-butoxy and t-butoxy.

The cycloalkyl groups referred to herein may represent, for example, cyclopropyl, cyclobutyl, cyclopentyl or cyclohexyl. A suitable cycloalkylalkyl group may be, for example, cyclopropylmethyl.

As used herein, the term "alkenyl" as a group or part of a group means that the group is straight or branched. Examples of suitable alkenyl groups include vinyl and allyl.

When used herein, the term "halogen" means fluorine, chlorine, bromine and iodine.

When used herein, the term "aryl" as a group or part of a group means a carbocyclic aromatic ring. Examples of suitable aryl groups include phenyl and naphthyl.

When used herein, the term "heteroaryl" as a group or part of a group means a 5- to 10-membered heteroaromatic ring system containing 1 to 4 heteroatoms selected from N, O and S. Particular examples of such groups include pyrrolyl, furanyl, thienyl, pyridyl, pyrazolyl, imidazolyl, oxazolyl, isoxazolyl, thiazolyl, isothiazolyl, pyrazinyl, pyrimidinyl, pyridazinyl, triazolyl, oxadiazolyl, thiadiazolyl, triazinyl, tetrazolyl, indolyl, benzothienyl, benzimidazolyl and quinolinyl.

When used herein, the term "Het" as a group or part of a group means a heteroaliphatic ring of 4 to 7 atoms, which ring may contain 1, 2 or 3 heteroatoms selected from N, O and S or a group S(O), S(O)$_2$, NH or $NC_{1-4}$alkyl.

Where a compound or group is described as "optionally substituted" one or more substituents may be present. Optional substituents may be attached to the compounds or groups which they substitute in a variety of ways, either directly or through a connecting group of which the following are examples: amine, amide, ester, ether, thioether, sulfonamide, sulfamide, sulfoxide, urea, thiourea and urethane. As appropriate an optional substituent may itself be substituted by another substituent, the latter being connected directly to the former or through a connecting group such as those exemplified above.

Specific compounds within the scope of this invention include those named in the Examples and Tables below and their pharmaceutically acceptable salts.

For use in medicine, the salts of the compounds of formula (I) will be non-toxic pharmaceutically acceptable salts. Other salts may, however, be useful in the preparation of the compounds according to the invention or of their non-toxic pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, fumaric acid, p-toluenesulfonic acid, maleic acid, succinic acid, acetic acid, citric acid, tartaric acid, carbonic acid, phosphoric acid or sulfuric acid. Salts of amine groups may also comprise quaternary ammonium salts in which the amino nitrogen atom carries a suitable organic group such as an alkyl, alkenyl, alkynyl or aralkyl moiety. Furthermore, where the compounds of the invention carry an acidic moiety, suitable pharmaceutically acceptable salts thereof may include metal salts such as alkali metal salts, e.g. sodium or potassium salts; and alkaline earth metal salts, e.g. calcium or magnesium salts.

The salts may be formed by conventional means, such as by reacting the free base form of the product with one or more equivalents of the appropriate acid in a solvent or medium in which the salt is insoluble, or in a solvent such as water which is removed in vacuo or by freeze drying or by exchanging the anions of an existing salt for another anion on a suitable ion exchange resin.

The present invention includes within its scope prodrugs of the compounds of formula (I) above. In general, such prodrugs will be functional derivatives of the compounds of formula (I) which are readily convertible in vivo into the required compound of formula (I). Conventional procedures for the selection and preparation of suitable prodrug derivatives are described, for example, in "Design of Prodrugs", ed. H. Bundgaard, Elsevier, 1985.

A prodrug may be a pharmacologically inactive derivative of a biologically active substance (the "parent drug" or "parent molecule") that requires transformation within the body in order to release the active drug, and that has improved delivery properties over the parent drug molecule. The transformation in vivo may be, for example, as the result of some metabolic process, such as chemical or enzymatic hydrolysis of a carboxylic, phosphoric or sulfate ester, or reduction or oxidation of a susceptible functionality.

The present invention includes within its scope solvates of the compounds of formula (I) and salts thereof, for example, hydrates.

The present invention also includes within its scope N-oxides of the compounds of formula (I).

The present invention also includes within its scope any enantiomers, diastereomers, geometric isomers and tautomers of the compounds of formula (I). It is to be understood that all such isomers and mixtures thereof are encompassed within the scope of the invention.

The present invention further provides a compound of formula (I) or a pharmaceutically acceptable salt thereof for use in therapy.

In another aspect, the invention provides the use of a compound of formula (I) as defined above, or a pharmaceutically acceptable salt thereof, for the manufacture of a medicament for treatment or prevention of infection by hepatitis C virus in a human or animal.

A further aspect of the invention provides a pharmaceutical composition comprising a compound of formula (I) as defined above, or a pharmaceutically acceptable salt thereof, in association with a pharmaceutically acceptable carrier. The composition may be in any suitable form, depending on the intended method of administration. It may for example be in the form of a tablet, capsule or liquid for oral administration, or of a solution or suspension for administration parenterally.

The pharmaceutical compositions optionally also include one or more other agents for the treatment of viral infections such as an antiviral agent, or an immunomodulatory agent such as α-, β- or γ-interferon.

In a further aspect, the invention provides a method of inhibiting hepatitis C virus polymerase and/or of treating or preventing an illness due to hepatitis C virus, the method involving administering to a human or animal (preferably mammalian) subject suffering from the condition a therapeutically or prophylactically effective amount of the pharmaceutical composition described above or of a compound of formula (I) as defined above, or a pharmaceutically acceptable salt thereof. "Effective amount" means an amount sufficient to cause a benefit to the subject or at least to cause a change in the subject's condition.

The dosage rate at which the compound is administered will depend on a variety of factors including the activity of the specific compound employed, the metabolic stability and length of action of that compound, the age of the patient, body weight, general health, sex, diet, mode and time of administration, rate of excretion, drug combination, the severity of the particular condition and the host undergoing therapy. Suitable dosage levels may be of the order of 0.02 to 5 or 10 g per day, with oral dosages two to five times higher. For instance, administration of from 10 to 50 mg of the compound per kg of body weight from one to three times per day may be in order. Appropriate values are selectable by routine testing. The compound may be administered alone or in combination with other treatments, either simultaneously or sequentially. For instance, it may be administered in combination with effective amounts of antiviral agents, immunomodulators, anti-infectives or vaccines known to those of ordinary skill in the art. It may be administered by any suitable route, including orally, intravenously, cutaneously and subcutaneously. It may be administered directly to a suitable site or in a manner in which it targets a particular site, such as a certain type of cell. Suitable targeting methods are already known.

An additional aspect of the invention provides a method of preparation of a pharmaceutical composition, involving admixing at least one compound of formula (I) as defined above, or a pharmaceutically acceptable salt thereof, with one or more pharmaceutically acceptable adjuvants, diluents or carriers and/or with one or more other therapeutically or prophylactically active agents.

The present invention also provides a process for the preparation of compounds of formula (I).

According to a general process (a), compounds of formula (I) may be prepared by internal ring closure of a compound of formula (II):

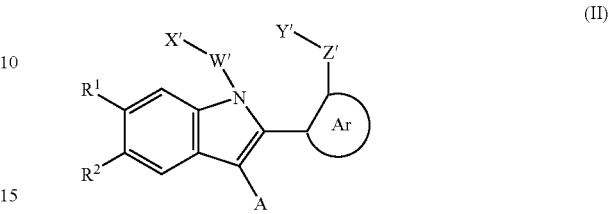

(II)

wherein $R^1$, $R^2$, A and Ar are as defined in relation to formula (I) and X' is converted to $-CR^{14}R^{15}-$ during or after the cyclisation reaction, W' is $-CH_2-$ or is converted to $-CH_2-$ during or after the cyclisation reaction, Y' is converted to Y during or after the cyclisation reaction, and Z' is Z or is converted to Z during or after the cyclisation reaction. W', X', Y' and Z' may be suitable activated precursors of groups $-CH_2-$, X, Y and Z respectively which can be converted into $-CH_2-$, X, Y and Z during the ring closure or after it using methods described in the accompanying Schemes and Examples or known to the person skilled in the art. For example, when Z is a bond, W', X', Y' and Z' are suitable precursors which are olefinic or can be converted to olefins in order to undergo a ring-closure methathesis reaction. Alternatively, when Z is $NR^{10}$, X' may be $CH_2$-halogen, $CH_2$-ester, $CH_2$-aldehyde, an epoxide or an aziridine group.

According to a general process (b), compounds of formula (I) may be prepared by internal ring closure of a compound of formula (III):

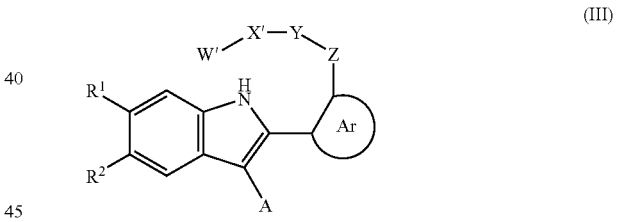

(III)

wherein $R^1$, $R^2$, A, Ar, Y and Z are as defined in relation to formula (I) and X' is $-CR^{14}R^{15}-$ or is converted to $-CR^{14}R^{15}-$ during or after the cyclisation reaction, and W' is converted to $-CH_2-$ during or after the cyclisation reaction. W' and X' may be suitable activated precursors of groups $-CH_2-$ and $-CR^{14}R^{15}-$ respectively which can be converted into $-CH_2-$ and $-CR^{14}R^{15}-$ during the ring closure or after it using methods described in the accompanying Schemes and Examples or known to the person skilled in the art. For example, W' may be $CH_2$-halogen or W' and X' together may be an epoxide or aziridine group. When W' is $CH_2$-halogen, such as $CH_2-Br$, the reaction is conveniently performed in the presence of a base, such as sodium hydroxide, in a suitable solvent, such as DMF. When W' and X' are an epoxide group, the reaction is conveniently performed in the presence of a base, such as sodium hydroxide, in a suitable solvent, such as DMF.

Compounds of formulae (II) and (III) are either known in the art or may be prepared by conventional methodology well known to one of ordinary skill in the art using, for instance, procedures described in the accompanying Schemes and Examples, or by alternative procedures which will be readily apparent.

Further details of suitable procedures will be found in the accompanying Schemes and Examples. For instance, compounds of formula (I) can be converted into other compounds of formula (I) using synthetic methodology well known in the art.

General Synthetic Schemes

In general, five synthetic schemes may be used to obtain the compounds of formula (I).

2-bromoindole intermediate (prepared as described in published International patent application WO2004/087714) was functionalized on the indole nitrogen to introduce precursor functionality W'/X' to either or both of the elements —$CH_2$/X of the tether. Pd-mediated cross-coupling methodology (eg, Suzuki, Stille etc) then brought in the C2 aromatic bearing precursor functionality Z'/Y' to either or both of the elements Z/Y of the tether. Functional group manipulation followed by ring closure afforded the tetracyclic system. Ester deprotection then yielded the target indole carboxylic acids, with the C2 aromatic tethered to the indole nitrogen.

Method A

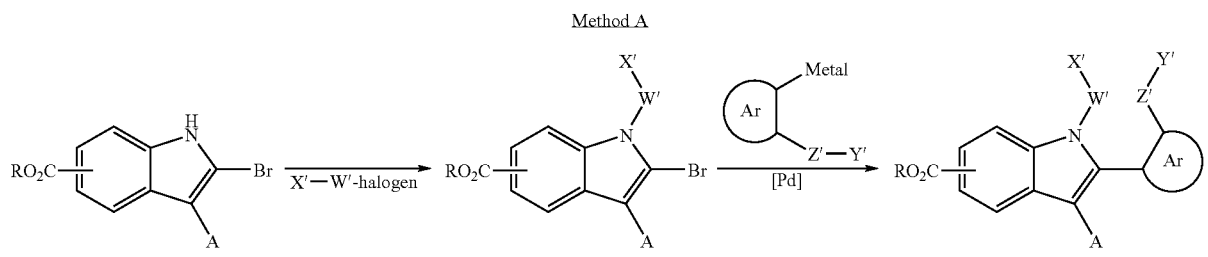

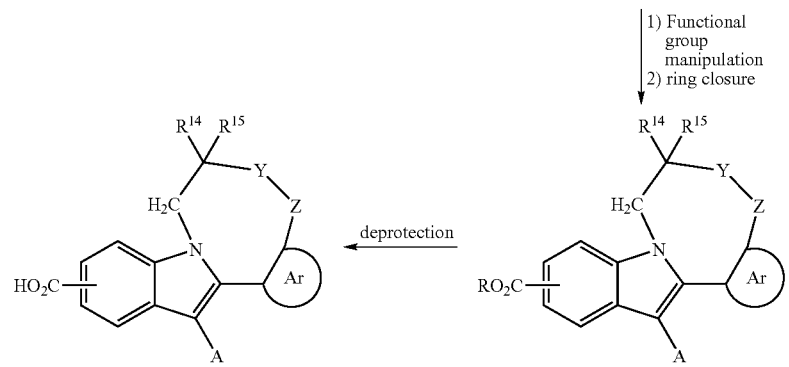

Method B

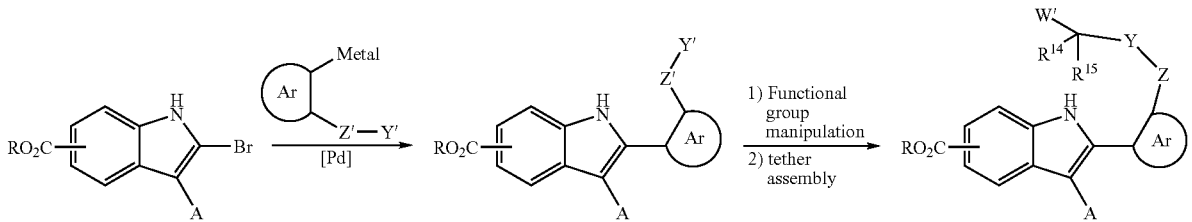

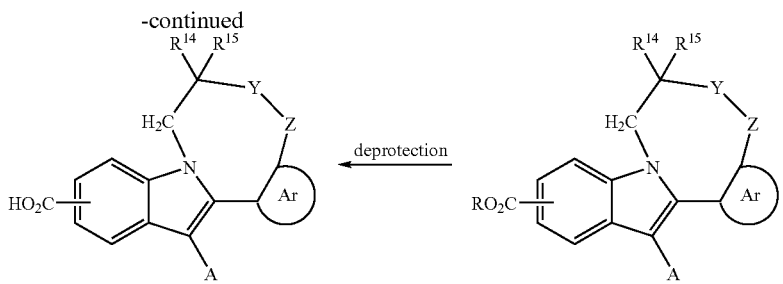

The C2 aromatic was introduced at the outset via Pd-mediated cross-coupling methodology (Suzuki, Stille etc). The tether was then built up, with cyclisation onto the indole nitrogen finally closing the ring. Ester deprotection then yielded the target indole carboxylic acids, with the C2 aromatic tethered to the indole nitrogen.

Method C

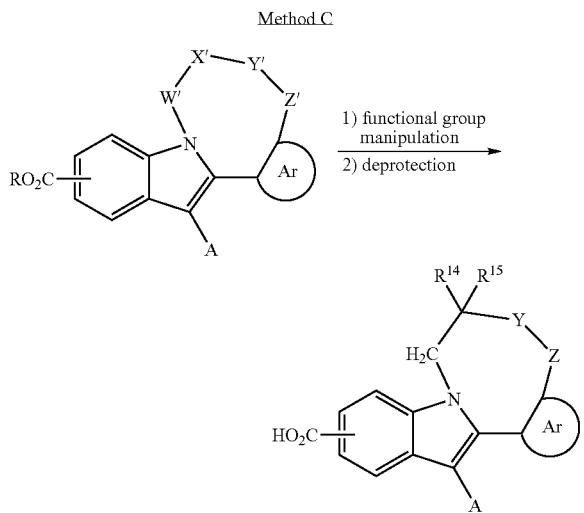

Fused tetracyclic intermediates arising from Methods A and B underwent manipulation of the functionality in the tether prior to ester deprotection to yield the target C2-tethered indole carboxylic acids.

Method D

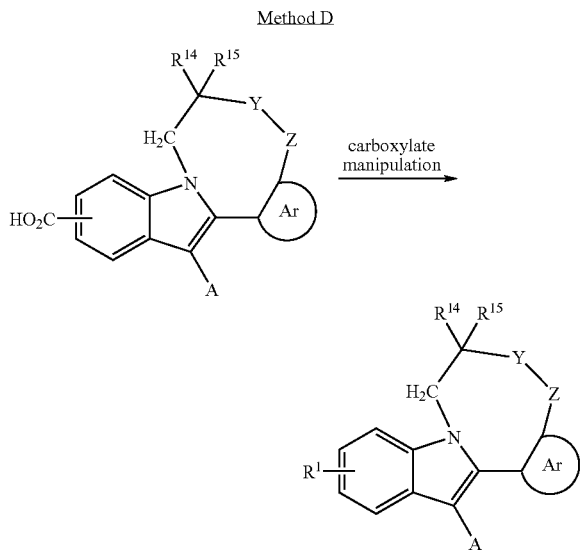

C2-tethered indole carboxylic acids arising from Methods A-C were further derivatised through manipulation of the carboxylate functionality to give compounds bearing a carboxylate replacement or carboxamide.

During any of the above synthetic sequences it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley & Sons, 3rd edition, 1999. The protecting groups may be removed at a convenient subsequent stage using methods known from the art.

The following Examples are illustrative of this invention.

The compounds of the invention were tested for inhibitory activity against the HCV RNA dependent RNA polymerase (NS5B) in an enzyme inhibition assay (example i)) and in a cell based sub-genomic replication assay (example ii)). The compounds have IC50's below 5 μM in the enzyme assay and several examples have EC50's below 2 μM in the cell based assay.

Compound names in the examples were generated using software from ACDLabs (version 6.0).

i) In-vitro HCV NS5B Enzyme Inhibition Assay

WO 96/37619 describes the production of recombinant HCV RdRp from insect cells infected with recombinant baculovirus encoding the enzyme. The purified enzyme was shown to possess in vitro RNA polymerase activity using RNA as template. The reference describes a polymerisation assay using poly(A) and oligo(U) as a primer or an heteropolymeric template. Incorporation of tritiated UTP or NTPs is quantified by measuring acid-insoluble radioactivity. This assay has been employed to screen the various compounds described above as inhibitors of HCV RdRp.

Incorporation of radioactive UMP was measured as follows. The standard reaction (50 μl) was carried out in a buffer containing 20 mM tris/HCl pH 7.5, 5 mM $MgCl_2$, 1 mM DTT, 50 mM NaCl, 0.03% N-octylglucoside, 1 μCi [$^3$H]-UTP (40 Ci/mmol, NEN), 10 μM UTP and 10 μg/ml poly(A) or 5 μM NTPs and 5 μg/ml heteropolymeric template. Oligo(U)$_{12}$ (1 μg/ml, Genset) was added as a primer in the assay working on Poly(A) template. The final NS5B enzyme concentration was 5 nM. The order of assembly was: 1) compound, 2) enzyme, 3) template/primer, 4) NTP. After 1 h incubation at 22° C. the reaction was stopped by adding 50 μl of 20% TCA and applying samples to DE81 filters. The filters were washed thoroughly with 5% TCA containing 1M $Na_2HPO_4/NaH_2PO_4$, pH 7.0, rinsed with water and then ethanol, air dried, and the filter-bound radioactivity was measured in the scintillation counter. Carrying out this reaction in the presence of various concentrations of each compound set out above allowed determination of $IC_{50}$ values by utilising the formula:

$$\% \text{ Residual activity} = 100/(1+[I]/IC_{50})^S$$

where [I] is the inhibitor concentration and "s" is the slope of the inhibition curve.

ii) Cell Based HCV Replication Assay

Cell clones that stably maintain subgenomic HCV replicon were obtained by transfecting Huh-7 cells with an RNA replicon identical to $I_{377}$neo/NS3-3'/wt described by Lohmann et al. (1999) (EMBL-genbank No. AJ242652), followed by selection with neomycin sulfate (G418). Viral replication was monitored by measuring the expression of the NS3 protein by an ELISA assay performed directly on cells grown in 96 wells microtiter plates (Cell-ELISA) using the anti-NS3 monoclonal antibody 10E5/24 (as described in published International patent application WO02/59321). Cells were seeded into 96 well plates at a density of $10^4$ cells per well in a final volume of 0.1 ml of DMEM/10% FCS. Two hours after plating, 50 µl of DMEM/10% FCS containing a 3× concentration of inhibitor were added, cells were incubated for 96 hours and then fixed for 10' with ice-cold isopropanol. Each condition was tested in duplicate and average absorbance values were used for calculations. The cells were washed twice with PBS, blocked with 5% non-fat dry milk in PBS+0.1% Triton X100+0.02% SDS (PBSTS) and then incubated o/n at 4° C. with the 10E5/24 mab diluted in Milk/PBSTS. After washing 5 times with PBSTS, the cells were incubated for 3 hours at room temperature with Fc specific anti-mouse IgG conjugated to alkaline phosphatase (Sigma), diluted in Milk/PBSTS. After washing again as above, the reaction was developed with p-Nitrophenyl phosphate disodium substrate (Sigma) and the absorbance at 405/620 nm read at intervals. For calculations, we used data sets where samples incubated without inhibitors had absorbance values comprised between 1 and 1.5. The inhibitor concentration that reduced by 50% the expression of NS3 ($IC_{50}$) was calculated by fitting the data to the Hill equation, $$\text{Fraction inhibition}=1-(A_i-b)/(A_0-b)=[I]^n/([I]^n+IC_{50})$$

where:
- $A_i$=absorbance value of HBI10 cells supplemented with the indicated inhibitor concentration.
- $A_0$ =absorbance value of HBI10 cells incubated without inhibitor.
- b=absorbance value of Huh-7 cells plated at the same density in the same microtiter plates and incubated without inhibitor.
- n=Hill coefficient.

iii) General Procedures

All solvents were obtained from commercial sources (Fluka, puriss.) and were used without further purification. With the exception of routine deprotection and coupling steps, reactions were carried out under an atmosphere of nitrogen in oven dried (110° C.) glassware. Organic extracts were dried over sodium sulfate, and were concentrated (after filtration of the drying agent) on rotary evaporators operating under reduced pressure. Flash chromatography was carried out on silica gel following published procedure (W. C. Still et al., J. Org. Chem. 1978, 43, 2923) or on commercial flash chromatography systems (Biotage corporation and Jones Flashmaster II) utilising pre-packed columns.

Reagents were usually obtained directly from commercial suppliers (and used as supplied) but a limited number of compounds from in-house corporate collections were utilised. In the latter case the reagents are readily accessible using routine synthetic steps that are either reported in the scientific literature or are known to those skilled in the art.

$^1$H NMR spectra were recorded on Bruker AM series spectrometers operating at (reported) frequencies between 300 and 600 MHz. Chemical shifts (δ) for signals corresponding to non-exchangeable protons (and exchangeable protons where visible) are recorded in parts per million (ppm) relative to tetramethylsilane and are measured using the residual solvent peak as reference. Signals are tabulated in the order: multiplicity (s, singlet; d, doublet; t, triplet; q, quartet; m, multiplet; b, broad, and combinations thereof); coupling constant(s) in hertz (Hz); number of protons. Mass spectral (MS) data were obtained on a Perkin Elmer API 100, or Waters MicroMass ZQ, operating in negative (ES$^-$) or positive (ES$^+$) ionization mode and results are reported as the ratio of mass over charge (m/z) for the parent ion only. Preparative scale HPLC separations were carried out on a Waters Delta Prep 4000 separation module, equipped with a Waters 486 absorption detector or on a Gilson preparative system. In all cases compounds were eluted with linear gradients of water and MeCN both containing 0.1% TFA using flow rates between 15 and 40 mL/min.

The following abbreviations are used in the examples, the schemes and the tables: Ac: acetyl; Ar: aryl; cat.: catalytic; dioxan(e): 1,4-dioxane; dppf: (1,1'-bisdiphenylphosphino) ferrocene; 1,2-DCE: 1,2-dichloroethane; DCM: dichloromethane; DIPEA: diisopropylethyl amine; DMAP: N,N-dimethylpyridin4-amine; DME: dimethoxyethane; DMF: dimethylformamide; DMSO: dimethylsulfoxide; DMP: Dess-Martin Periodinane; EDAC, HCl: 1-ethyl-(3-dimethylaminopropyl)carbodiimide HCl salt; eq.: equivalent(s); Et$_3$N: triethylamine; EtOAc: ethyl acetate; Et$_2$O: diethyl ether; EtOH: ethanol; h: hour(s); Et$_3$SiH: triethylsilane; HOAc: acetic acid; HATU: O-(7-azabenzotriazol-1-yl)-N,N,N',N'-tetramethyluronium hexafluorophophate; Me: methyl; MeCN: acetonitrile; MeOH: methanol; min: minutes; MS: mass spectrum; NBS: N-bromo succinimide; PE: petroleum ether; Ph: phenyl; quant.: quantitative; RP-BPLC: reversed phase high-pressure liquid chromatography; RT: room temperature; sec: second(s); SFC: Super-critical fluid chromatography; s. s.: saturated solution; TBTU: O-benzotriazol-1-yl-N,N,N',N'-tetramethyluronium tetrafluoroborate; TFA: trifluoroacetic acid; THF: tetrahydrofuran; THP: terhahydropyranyl; TMS: trimethylsilyl.

Reagents: Zhan catalyst I ([1,3-bis(2,4,6-trimethylphenyl)-4,5-dihydro-imidazol-2-ylidene]-[4-chloro-1-isopropxy-benzylidine]ruthenium-dichloride: commercially available from ZannanPharma Ltd. (www.zannanpharma.com); methyl (aminosulfonyl)acetate was prepared in analogous fashion to related esters of aminosulfonyl acetic acid: eg, Tetrahedron Lett. 1989, 30 (22), 2869; Bull. Soc. Chim. France 1975, 3, 807.

EXAMPLE 1

Preparation of 13-cyclohexyl-5-(2-pyrrolidin-1-ylethoxy)-6,7-dihydro-5H-indolo[2,1-a][2]benzazepine-10-carboxylic Acid and 13-cyclohexyl-6-(2-pyrrolidin-1-ylethoxy)-6,7-dihydro-5H-indolo[2,1-a][2]benzazepine-10-carboxylic Acid Step 1: Methyl 3-cyclohexyl-2-(2-vinylphenyy)-1H-indole-6-carboxylate Methyl 2-bromo-3-cyclohexyl-1H-indole-6-carboxylate (prepared as described in WO 2004/087714) and (2-vinylphenyl)boronic acid (1.5 eq) were dissolved in dioxane (0.07 M) and 2M aqueous Na$_2$CO$_3$ (6 eq) was added. The solution was degassed by bubbling argon, Pd(PPh$_3$)$_2$Cl$_2$ (0.2 eq) was added, and the reaction mixture was refluxed for 1 h; after cooling, EtOAc was added, and the solution washed with water and brine, dried over Na$_2$SO$_4$ and concentrated in vacuo. The title compound was isolated by chromatography (PE/EtOAc 9:1) in 91% yield; MS (ES$^+$) m/z 360 (M+H)$^+$.

Step 2: Methyl 1-allyl-3-cyclohexyl-2-(2-vinylphenyl)-1H-indole-6-carboxylate

To a 0.3M solution of methyl 3-cyclohexyl-2-(2-vinylphenyl)1H-indole-6-carboxylate in dry DMF, 60% NaH (1.5 eq) in mineral oil was added at 0° C., after 1 h allyl bromide (1.5 eq) was added and the suspension was stirred at RT for 2 h. The mixture was diluted with EtOAc, washed with 1N HCl, water and brine, dried over $Na_2SO_4$ and concentrated in vacuo to give the title compound (100% as crude); MS (ES$^+$) m/z 400 (M+H)$^+$.

Step 3: Methyl 13-cyclohexyl-7H-indolo[2,1-a]2benzazepine-10-carboxylate

Crude methyl 1-allyl-3-cyclohexyl-2-(2-vinylphenyl)1H-indole-6-carboxylate was dissolved in DCM (0.02M) and treated with Zhan catalyst I (0.3 eq) at 35° C. for 1 h. NEt$_3$ (7 eq) were added and the solvent was removed in vacuo. The residue was purified by chromatography (PE/EtOAc 95:5) to afford the title compound (84%); MS (ES$^+$) m/z 372 (M+H)$^+$.

Step 4: 13-cyclohexyl-5-(2-pyrrolidin-1-ylethoxy)-6,7-dihydro-5H-indolo[2,1-a ][2]benzazepine-10-carboxylic Acid and 13-cyclohexyl-6-(2-pyrrolidin-1-ylethoxy)-6,7-dihydro-5H-indolo[2,1- a][2]benzazepine-10-carboxylic Acid BH$_3$.Me$_2$S (1.6 eq, 2M solution in THF) was added to a 0.2M solution of methyl 13-cyclohexyl-7H-indolo[2,1-a][2]benzazepine-10-carboxylate in THF, and the mixture was stirred for 2 h at RT; 3M aq NaOH (3 eq) and 35% H$_2$O$_2$ (3 eq) were added at 0° C., and stirring was continued overnight at RT. After dilution with saturated aqueous NaHCO$_3$ the aq. phase was. extracted with EtOAc, the organic phase was washed with water and brine, dried over Na$_2$SO$_4$ and concentrated in vacuo to give a 4:1 mixture of methyl 13-cyclohexyl-5-hydroxy-6,7-dihydro-5H-indolo[2,1-a][2]benzazepine-10-carboxylate and methyl 13-cyclohexyl-6-hydroxy-6,7-dihydro-5H-indolo[2,1-a][2]benzazepine-10-carboxylate. The foregoing crude was dissolved in toluene (20 ml/mmol), 40% aq NaOH (15 eq) and tetrabutyl ammonium bromide (0.25 eq) were added, and the mixture was stirred for 30 min. 1-(2-chloroethyl)pyrrolidine hydrochloride (3 eq) was then added and the resulting mixture heated at 70° C. for 1 day; evaporation to dryness gave a residue from which the two regioisomers were separated by RP-HPLC (combined overall yield 32%) (Conditions: Column: Waters X-TERRA MS C18, 10 micron, 19×150 mm; Gradient: A: H$_2$O+0.1% TFA; B: MeCN+0.1% TFA; 75% A isocratic for 3 min, linear to 20% A in 12 min).

13-Cyclohexyl-5-(2-pyrrolidin-1-ylethoxy)-6,7-dihydro-5H-indolo[2,1-a][2]benzazepine-10-carboxylic acid (major): $^1$H NMR (400 MHz, DMSO, 300 K) δ 1.16-1.51 (4H, m), 1.58-2.06 (12H, m), 2.82-2.90 (2H, m), 3.00-3.21 (3H, m), 3.45-3.75 (5H, m), 4.234.73 (2H, m), 7.46-7.64 (5H, m), 7.83-7.87 (1H, m), 8.13 (1H, s), 12.30 (1H, bs); MS (ES$^+$) m/z 473 (M+H)$^+$.

13-Cyclohexyl-6-(2-pyrrolidin-1-ylethoxy)-6,7-dihydro-5H-indolo[2,1-a][2]benzazepine-10-carboxylic acid (minor): $^1$H NMR (400 MHz, DMSO, 330 K)δ 1.16-1.56 (4H, m), 1.68-2.26 (12H, m), 2.80-2.93 (1H, m), 2.98-3.18 (3H, m), 3.46-3.68 (4H, m), 3.78-3.83 (1H, m), 4.04-4.07 (1H, m), 4.18-4.37 (1H, m), 4.75-4.90 (1H, m), 7.43-7.49 (4H, m), 7.65 (1H, dd, J 8.6, 1.1), 7.88 (1H, d, J 8.6), 8.13-8.22 (1H, m), 11.44 (1H, bs); MS (ES$^+$) m/z 473 (M+H)$^+$.

EXAMPLE 2

Preparation of 13-cyclohexyl-5-[[2-(dimethylamino)ethyl]-(methyl)amino]-6,7-dihydro-5H-indolo[2,1-a][2]benzazepine-10-carboxylic Acid PBr$_3$ (0.5 eq) was added at 0° C. to a 0.2M solution of a mixture of the two regioisomers methyl 13-cyclohexyl-5-hydroxy-6,7-dihydro-5H-indolo[2,1-a][2]benzazepine-10-carboxylate and methyl 13-cyclohexyl-6-hydroxy-6,7-dihydro-5H-indolo[2,1-a][2]benzazepine-10-carboxylate (prepared as described in Example 1, Step 4) in DCM, and the mixture was stirred at RT for 2 h. The reaction mixture was diluted with EtOAc, washed with water and brine, dried over Na$_2$SO$_4$ and concentrated in vacuo to give the mixture of methyl 5-bromo-13-cyclohexyl-6,7-dihydro-5H-indolo[2,1-a][2]benzazepine-10-carboxylate and methyl 6-bromo-13-cyclohexyl-6,7-dihydro-5H-indolo[2,1-a][2]benzazepine-10-carboxylate that was dissolved in MeCN and treated with N,N,N'-trimethylethane-1,2-diamine (8 eq) at 55° C. for 3 h; evaporation in vacuo to dryness gave crude methyl 13-cyclohexyl-5-[methyl(2-pyrrolidin-1-ylethyl)amino]-6,7-dihydro-5H-indolo[2,1-a][2]benzazepine-10-carboxylate together with the unreacted methyl 6-bromo-13-cyclohexyl-6,7-dihydro-5H-indolo[2,1-a][2]benzazepine-10-carboxylate. Hydrolysis of the foregoing mixture of methyl esters was done with 1M aqueous KOH (6 eq) in dioxane (0.1M) at 60° C.; the reaction was complete in 2 h, and the title compound was obtained in 49% yield after RP-HPLC purification and lyophilisation (Conditions: Column: Waters X-TERRA MS C18, 10 micron, 19×150 mm; flow: 20 ml/min; Gradient: A: H$_2$O+0.1% TFA; B: MeCN+0.1% TFA; 75% A isocratic for 3 min, linear to 20% A in 12 min).

$^1$H NMR (400 MHz, DMSO, 300 K) δ 1.15-1.78 (6H, m), 1.82-2.09 (5H, m), 2.19-2.30 (3H, m), 2.55-2.7 (2H, m), 2.78 (6H, s), 2.80-2.96 (1H, m), 3.13-3.40 (4H, m), 4.604.66 (1H, m), 7.40 (1H, d, J7.2), 7.47-7.56 (2H, m), 7.62 (1H, d, J8.3), 7.75 (1H, d, J7.2), 7.87 (1H, d, J8.3), 8.14 (1H, s); MS (ES$^+$) m/z 460 (M+H)$^+$.

EXAMPLE 3

Preparation of 13-cyclohexyl-5-[(2-pyrrolidin-1-ylethyl)amino]-6,7-dihydro-5H-indolo[2,1-a][2]benzazepine-10-carboxylic Acid A 0.03M solution of 5-bromo-13-cyclohexyl-6,7-dihydro-5H-indolo[2,1-a][2]benzazepine-10-carboxylate (prepared as in Example 2) in MeCN was treated with (2-pyrrolidin-1-ylethyl)amine (5 eq) at 55° C. for 4 h; evaporation in vacuo to dryness gave crude methyl 13-cyclohexyl-5-[(2-pyrrolidin-1-ylethyl)amino]-6,7-dihydro-5H-indolo[2,1-a][2]benzazepine-10-carboxylate. Hydrolysis of the foregoing methyl ester was done with 1M aqueous KOH (6 eq) in dioxane (0.1M) at 60° C.; the reaction was complete in 2 h, and the title compound was obtained in 24% yield after RP-HPLC purification and lyophilisation (Conditions: Column: Waters X-TERRA MS C18, 10 micron, 19×150 mm; Gradient: A: H$_2$O+0.1% TFA; B: MeCN+0.1% TFA; 75% A isocratic for 3 min, linear to 20% A in 12 min).

$^1$H NMR (400 MHz, DMSO, 300 K) δ 1.15-1.77 (7H, m), 1.90-2.17 (10H, m), 2.78-2.91 (2H, m), 3.40-3.59 (7H, m), 4.11-4.16 (1H, m), 4.75-4.81 (1H, m), 7.51-7.66 (5H, m), 7.92 (1H, d, J 8.5), 8.20 (1H, s); MS (ES$^+$) m/z 472 (M+H)$^+$.

EXAMPLE 4

Preparation of 13-cyclohexyl-5-[methyl(2-pyrrolidin-1-ylethyl)amino]-6,7-dihydro-5H-indolo[2,1-a][2]benzazepine-10-carboxylic Acid Methyl 13-cyclohexyl-5-[(2-pyrrolidin-1-ylethyl)amino]-6,7-dihydro-5H-indolo[2,1-a][2]benzazepine-10-carboxylate (prepared as in Example 3) was dissolved in DCM and the pH adjusted to 6 with AcOH; 37% aq HCHO and, after 30 min NaCNBH$_3$ (3 eq), were added and the mixture was stirred at RT overnight. The reaction mixture was diluted with EtOAc and washed with 1N NaOH and brine, dried and evaporated affording methyl 13-cyclohexyl-5-[methyl(2-pyrrolidin-1-ylethyl)amino]-6,7-dihydro-5H-indolo[2,1-a][2]benzazepine-10-carboxylate. Hydrolysis of the foregoing methyl ester was done with 1M aqueous KOH (6 eq) in dioxane (0.1M) at 60 ° C.; the reaction was complete in 2 h, and the title compound was obtained in 29% yield after RP-HPLC purification and lyophilisation (Conditions: Column: Waters X-TERRA MS C18, 10 micron, 19×150 mm; Gradient: A: $H_2O+0.1\%$ TFA; B: MeCN+0.1% TFA; 75% A isocratic for 3 min, linear to 20% A in 12 min).

$^1$H NMR (400 MHz, DMSO, 300 K) δ 1.16-1.77 (8H, m), 1.80-2.11 (8H, m), 2.19-2.31 (2H, m), 2.61-2.87 (5H, m), 2.98-3.41 (7H, m), 4.54-4.66 (1H, m), 7.42 (1H, d, J 8.1), 7.47-7.54 (2H, m), 7.63 (1H, d, J 8.3), 7.69-7.75 (1H, m), 7.86 (1H, d, J 8.3), 8.12 (1H, s); MS (ES$^+$) m/z 486 (M+H)$^+$.

EXAMPLE 5

Preparation of 13-cyclohexyl-6-{[2-(dimethylamino)ethyl]amino}-6,7-dihydro-5H-indolo[2,1-a][2]benzazepine-10-carboxylic Acid Step 1: Methyl 13-cyclohexyl-5,6-dihydroxy-6,7-dihydro-5H-indole[2,1-a][2]benzazepine-10-carboxylate A solution (0.11 M) of methyl 13-cyclohexyl-7H-indolo[2,1-a][2]benzazepine-10-carboxylate (prepared as in Example 1, Step 3) in acetone/THF/H$_2$O (1/1/1) was treated with N-methylmorpholine-N-oxide (1.2 eq), followed by OsO$_4$ (4% wt in H$_2$O) (0.1 eq) and left stirring at RT overnight. The clear solution was then treated with 10% wt Na$_2$SO$_3$ and left stirring for 30 min, then diluted with H$_2$O and extracted with EtOAc. The organic phase was washed with brine, dried over Na$_2$SO$_4$ and evaporated in vacuo to give the clean title compound as a creamy solid; MS (ES$^+$) mn/z 406 (M+H)$^+$.

Step 2: Methyl 10-cyclohexyl-2-oxo-3a,14b-dihydro-4H-[1,3]dioxolo[4,5-d]indolo[2,1-a][2]benzazepine-7-carboxylate A solution (0.05 M) of methyl 13-cyclohexyl-5,6-dihydroxy-6,7-dihydro-5H-indole[2,1-a][2]benzazepine-10-carboxylate in DCM was treated with Et$_3$N(4 eq), and cooled to −50° C. Triphosgene (0.4 eq) was added and the solution allowed to warm to RT over 30 min. After 2 h at RT, satd. NaHCO$_3$ was added and the solution extracted with EtOAc. The organic phase was washed with H$_2$O, brine, dried (Na$_2$SO$_4$) and evaporated in vacuo to leave the clean title compound; MS (ES$^+$) m/z 432.3 (M+H)$^+$.

Step 3: Methyl 13-cyclohexyl-6-hydroxy-6,7-dihydro-5H-indolo[2,1-a][2]benzazepine-10-carboxylate A solution (0.02 M) of methyl 10-cyclohexyl-2-oxo-3a,14b-dihydro-4H-[1,3]dioxolo[4,5-d]indolo[2,1-a][2]benzazepine-7-carboxylate in acetone/MeOH (3/1) was treated with Raney-Ni (slurry in water) and the vigorously stirred reaction mixture was hydrogenated at 1 atm H$_2$. After 48 h the solid was filtered and the filtrates evaporated in vacuo to leave the clean title compound; MS (ES$^+$) m/z 390.3 (M+H)$^+$.

Step 4: 13-cyclohexyl-6-{[2-(dimethylamino)ethyl]amino}-6,7-dihydro-5H-indolo[2,1-a][2]benzazepine-10-carboxylic Acid A solution (0.05 M) of methyl 13-cyclohexyl-6-hydroxy-6,7-dihydro-5H-indolo[2,1-a][2]benzazepine-10-carboxylate in DCM was treated with DMP (1.3 eq) at 0° C. and left warming to RT and then stirred for 2 h under nitrogen. The solution was then diluted with EtOAc and washed with satd. NaHCO$_3$, water, brine, dried over Na$_2$SO$_4$ and evaporated in vacuo to afford methyl 13-cyclohexyl-6-oxo-6,7-dihydro-5H-indolo[2,1-a][2]benzazepine-10-carboxylate. The crude material was dissolved in 1,2-DCE (0.05 M), 2-dimethylamino-ethylamine was added and the pH adjusted to 6 with AcOH and the solution left stirring for 30 min. NaBH(OAc)$_3$ was added and the solution was left stirring at RT overnight. After diluting with EtOAc, the organic phase was washed with NaOH (1N), water, brine, dried over Na$_2$SO$_4$ and evaporated in vacuo to afford methyl 13-cyclohexyl-6-{[2-(dimethylamino)ethyl]amino}-6,7-dihydro-5H-indolo[2,1-a][2]benzazepine-10-carboxylate. Hydrolysis of the foregoing methyl ester was done with 1M aqueous KOH (6 eq) in dioxane (0.1M) at 60 ° C.; the reaction was complete in 2 h, and the title compound was obtained in 31% yield after RP-HPLC purification and lyophilisation (Conditions: Column: Waters X-TERRA MS C18, 10 micron, 19×150 mm; Gradient: A: H$_2$O+0.1% TFA; B: MeCN+0.1% TFA; 75% A isocratic for 3 min, linear to 20% A in 12 min).

$^1$H NMR (400 MHz, DMSO, 300 K) δ 1.16-1.59 (4H, m), 1.61-2.12 (6H, m), 2.74-2-98 (8H, m), 3.12-3.43 (7H, m), 4.69-4.73 (1H, m), 7.49-7.58 (4H, m), 7.67-7.73 (1H, m), 7.90-7.93 (1H, m), 8.24 (1H, bs); MS (ES$^+$) m/z 446.4 (M+H)$^+$.

EXAMPLE 6

Preparation of 13-cyclohexyl-6-{[2-(dimethylamino)ethyl][(methyl)amino]}-6,7-dihydro-5H-indolo[2,1-a][2]benzazepine-10-carboxylic Acid Methyl 13-cyclohexyl-6-{[2-(dimethylamino)ethyl]amino}-6,7-dihydro-5H-indolo[2,1-a][2]benzazepine-10-carboxylate (prepared as in Example 5, Step 4) was dissolved in DCM (0.07 M) and pH adjusted to 6 with AcOH; 37% aq HCHO and, after half an hour NaCNBH$_3$ (3 eq), were added and the mixture was stirred at RT overnight. The reaction mixture was diluted with EtOAc and washed with 1N NaOH and brine, dried and evaporated affording methyl 13-cyclohexyl-6-{[2-(dimethylamino)ethyl][(methyl) amino]}-6,7-dihydro-5H-indolo[2,1-a][2]benzazepine-10-carboxylate. Hydrolysis of the foregoing methyl ester was done with 1M aqueous KOH (6 eq) in dioxane (0.1M) at 60 ° C.; the reaction was complete in 2 h, and the title compound was obtained in 20% yield after RP-HPLC purification and lyophilisation (Conditions: Column: Waters X-TERRA MS C18, 10 micron, 19×150 mm; Gradient: A: H$_2$O+0.1% TFA; B: MeCN+0.1% TFA; 75% A isocratic for 3 min, linear to 20% A in 12 min).

$^1$H NMR (400 MHz, DMSO, 300K) δ 1.16-1.59 (4H, m), 1.61-2.12 (6H, m), 2.74-2-98 (11H, m), 3.18-3.30 (1H, m), 3.50-3.69 (4H, m), 3.91-3.99 (1H, m), 4.214.30 (1H, m), 4.89-5.01 (1H, m), 7.39-7.58 (4H, m), 7.64-7.71 (1H, m), 7.92-7.99 (1H, m), 8.23-8.32 (1H, bs); MS (ES$^+$) m/z 460.5 (M+H)$^+$.

EXAMPLE 7

Preparation of 12-cyclohexyl-4-(2-pyrrolidin-1-ylethoxy)-5,6-dihydro-4H-thieno[2',3':3,4]azepino[1,2-a]indole-9-Carboxylic acid and 12-cyclohexyl-5-(2-pyrrolidin-1-ylethoxy)-5,6-dihydro-4H-thieno[2',3':3,4]azepino[1,2-a]indole-9-carboxylic Acid Step 1: Methyl 3-cyclohexyl-2-(3-formyl-2-thienyl)1H-indole-6-carboxylate Methyl 2-bromo-3-cyclohexyl1H-indole-6-carboxylate (prepared as described in published International patent application WO 2004/087714), (3-formyl-2-thienyl)boronic acid (1.2 eq), spray-dried KF (5 eq) and Pd(tBu$_3$P)$_2$ (0.2 eq) were dissolved in dioxane (0.15 M); the reaction mixture was stirred under N$_2$ at RT for 4 h, then more KF, boronic acid and catalyst were added and stirring was continued overnight. All volatiles were evaporated in vacuo and the title compound was isolated by flash chromatography (PE/EtOAc 8:2). Yield 99%; MS (ES+) m/z 368 (M+H)+.

Step 2: Methyl 3-cyclohexyl-2-(3-vinyl-2-thienyl)-1H-indole-6-carboxylate Tebbe reagent (0.5M in toluene) was added dropwise, at 0° C. to a 0.2M solution of methyl 3-cyclohexyl-2-(3-formyl-2-thienyl)-1H-indole-6-carboxylate in dry THF; after 30 min the mixture was diluted with Et$_2$O and quenched with 0.1M aq NaOH. After 5 min Na$_2$SO$_4$ and Celite™ were added and the mixture filtered; the filtrate was concentrated in vacuo and the residue purified by flash chromatography (PE/EtOAc 10:1). Yield 34%; MS (ES+) m/z 366 (M+H)+.

Step 3: Methyl 1-allyl-3-cyclohexyl-2-(3-vinyl-2-thienyl)-1H-indole-6-carboxylate To a 0.1M solution of methyl 3-cyclohexyl-2-(3-vinyl-2-thienyl)1H-indole-6-carboxylate in dry DMF, 60% NaH (1.2 eq) in mineral oil was added; when gas evolution had ceased, allyl bromide (1.4 eq) was added, and the suspension was stirred at RT for 30 min. All volatiles were evaporated and the title compound was isolated by flash chromatography (PE/EtOAc 10:1). Yield 77%.

$^1$H NMR (400 MHz, CDCl$_3$, 300 K) δ 1.28-1.90 (m, 1OH), 2.60-2.69 (m, 1H), 3.97 (s, 3H), 4.52 (d$_b$, J 16.6, 1H), 4.63 (d$_b$, J 16.6, 1H), 4.89 (d, J 17.2, 1H), 5.08 (d, J 10.1, 1H), 5.19 (d, J 11.1, 1H), 5.59 (d, J 17.4, 1H), 5.76-5.84 (m, 1H), 6.35 (dd, J17.4, 11.1, 1H), 7.39-7.46 (m, 2H), 7.80 (d, J 8.6, 1H), 7.84 (d, J 8.6, 1H), 8.08 (s, 1H).

Step 4: Methyl 12-cyclohexyl-6H-thieno[2',3',:3,4]azepino[1,2-a]indole-9-carboxylate Methyl 1-allyl-3-cyclohexyl-2-(3-vinyl-2-thienyl)1H-indole-6-carboxylate was dissolved in DCM (0.03M) and treated with Zhan catalyst I (5 mg per 100 mg of substrate) at 35° C. for 2 h. After removal of solvent the residue was purified by flash chromatography (PE/EtOAc 12:1) to afford the title compound (90%); MS (ES+) m/z 378 (M+H)+.

Step 5: 12-cyclohexyl-4-(2-pyrrolidin-1-ylethoxy)-5,6-dihydro-4H-thieno[2',3':3,4]azepino[1,2-a]-indole-9-carboxylic Acid and 12-cyclohexyl-5-(2-pyrrolidin-1-ylethoxy)-5,6-dihydro-4H-thieno[2',3':3,4]azepino[1,2-a]indole-9-carboxylic Acid BH$_3$Me$_2$S (1.6 eq, 2M solution in THF) was added to a 0.1M solution of methyl 12-cyclohexyl-6H-thieno[2',3':3,4] azepino[1,2-a]indole-9-carboxylate in dry THF, and the mixture was stirred for 3 h at RT; 3M aq NaOH (3 eq) and 35% H$_2$O$_2$ (3.5 eq) were added at 0° C., and stirring was continued for 2 h at RT. After dilution with EtOAc, the mixture was extracted with sat. aqueous NaHCO$_3$ and with brine. The organic phase was dried Na$_2$SO$_4$ and evaporated in vacuo to give a 4:1 mixture of methyl 12-cyclohexyl-4-hydroxy-5,6-dihydro4H-thieno[2',3':3,4]azepino[1,2-a]indole-9-carboxylate and methyl 12-cyclohexyl-5-hydroxy-5,6-dihydro4H-thieno[2',3':3,4]azepino[1,2-a]indole-9-carboxylate. This crude mixture was dissolved in toluene (0.07M), tetrabutylammonium bromide (0.25 eq) and 40% aq. NaOH (15 eq) were added, and the mixture was warmed to 70° C. After stirring for half an hour at this temperature 1-(2-chloroethyl)pyrrolidine hydrochloride (3 eq) was added and heating was continued at 70° C. for 2 days. All volatiles were evaporated in vacuo and the products isolated by RP-HPLC (combined overall yield 27%). (Conditions: Column: Waters X-TERRA MS C18, 7 um, 19×150 mm; Gradient: A: H$_2$O+0.1% TFA; B: MeCN+0.1% TFA; 99% A to 1% A in 15 min).

12-Cyclohexyl-4-(2-pyrrolidin-1-ylethoxy)-5,6-dihydro4H-thieno[2',3':3,4]azepino[1,2-a]indole-9-carboxylic acid (major): $^1$H NMR (400 MHz, DMSO, 300 K) δ 1.35-1.43 (m, 3H), 1.59-1.85 (m, 9H), 1.97-2.05 (m, 2H), 2.25-2.32 (m, 1H), 2.60-2.68 (m, 1H), 2.79-2.90 (m, 2H), 3.17-3.26 (m, 4H), 3.30-3.36 (m, 1H), 3.51-3.64 (m, 2H), 4.09-4.22 (m, 2H), 4.75 (t, J 6.14, 1H), 7.31 (d, J 5.26, 1H), 7.60 (dd, J 8.55, 1H), 7.77 (d, J 5.26, 1H), 7.85 (d, J 8.55, 1H), 8.14 (s, 1H), 9.44 (S$_b$, 1H); MS (ES+) m/z 479.4 (M+H)+.

12-Cyclohexyl-5-(2-pyrrolidin-1-ylethoxy)-5,6-dihydro4H-thieno[2',3':3,4]azepino[1,2-a]indole-9-carboxylic acid (minor): $^1$H NMR (400 MHz, DMSO, 330 K) o 1.27-1.38 (m, 3H), 1.69-2.32 (m, 11H), 2.57-2.62 (m, 1H), 3.03-3.18 (m, 4H), 3.38-3.56 (m, 4H), 3.85-3.90 (m, 1H), 3.94-4.00 (m, 1H), 4.03-4.08 (m, 1H), 4.31-4.35 (m, 2H), 7.20 (d, J 5.04, 1H), 7.63 (dd, J 8.55, 1H), 7.70 (d, J 5.05, 1H), 7.86 (d, J 8.55, 1H), 8.16 (s, 1H), 9.53 (S$_b$, 1H); MS (ES+) m/z 479.4 (M+H)+.

EXAMPLE 8

14-cyclohexyl-5-[2-(dimethylamino)ethyl]-6-oxo-5,6,7,8-tetrahydroindolo[1,2-e][1,5]benzodiazocine-11-carboxylic Acid Step 1: 3-[2-bromo-3-cyclohexyl-6-(methoxycarbonyl)-1H-indol-1-yl]propanoic Acid 3.5 eq of NaH (60% dispersion in mineral oil) was added to a solution of methyl 2-bromo-3-cyclohexyl-1H-indole-6-carboxylate (prepared as described in published International patent application WO 2004/087714, from commercially available methyl indole-6-carboxylate) in DMF (0.2 M) and the solution allowed to stir at RT for 1 h. Then 1.1 eq of 3-bromopropanoic acid were added and the mixture stirred at RT for 2 h. DMF was concentrated in vacuo and the residue taken up in EtOAc. The organic phase was washed with 1 N HCl and then brine before being dried over Na$_2$SO$_4$, filtered and the solvent evaporated in vacuo. The title compound was used crude in the next step; MS (ES+) m/z 408 (M+H)+, m/z 410 (M+H)+

Step 2: Methyl 2-bromo-3-cyclohexyl-1-(3-methoxy-3-oxopropyl)-1H-indole-6-carboxylate 1.6 eq of (Trimethylsilyl)diazomethane (2 M solution in hexanes) was added dropwise to a solution of 3-[2-bromo-3-cyclohexyl-6-(methoxycarbonyl)-1H-indol-1-yl]propanoic acid in a mixture toluene:MeOH (7:3; 0.2 M) and the solution allowed to stir at RT for 1 h. Excess (Trimethylsilyl)diazomethane was quenched with acetic acid and then the solution was concentrated in vacuo. The crude was purified by flash chromatography (Biotage cartridge Si4OS, 1:9 EtOAc/PE) to afford the title compound in 63% yield (over two steps). MS (ES+) m/z 422 (M+H)+, m/z 424 (M+H)+

Step 3: Methyl 2-{2-[(tert-butoxycarbonyl)amino]phenyl}-3-cyclohexyl-1-(3-methoxy-3-oxopropyl)-1H-indole-6-carboxylate To a solution of methyl 2-bromo-3-cyclohexyl-1-(3-methoxy-3-oxopropyl)-1H-indole-6-carboxylate in dioxane (0.15 M) was added Na$_2$CO$_3$ (4 eq, 2 M aqueous solution), tert-butyl [2-(4,4,5,5-tetramethyl-1,3,2-dioxaborolan-2-yl)phenyl]carbamate (1.5 eq) and bis(triphenylphosphine)palladium(II) dichloride (0.2 eq). The mixture was heated at reflux for 45 mins. The reaction mixture was filtered and then the filtrate was diluted with EtOAc. The organic phase was washed with H$_2$O, brine and dried over Na$_2$SO$_4$ before being filtered and concentrated in vacuo. The crude was purified by flash chromatography (Biotage cartridge Si65i, 1:9 EtOAc/PE) to give the title compound as a white solid (60%); MS (ES+) m/z 535 (M+H)+.

Step 4: 3-[2-{2-[(tert-butoxycarbonyl)amino]phenyl}-3-cyclohexyl-6-(methoxycarbonyl)-1H-indol-1-yl]1propanoic Acid 1.1 eq of lithium hydroxide monohydrate was added to a solution of methyl 2-{2-[(tert-butoxycarbonyl) amino]phenyl}-3-cyclohexyl-1-(3-methoxy-3-oxopropyl)-1H-indole-6-carboxylate in a mixture THF:H$_2$O (4:1; 0.1 M). The mixture was stirred at RT for 1.5 h. The reaction was quenched with 1 N HCl and the solvent evaporated in vacuo. The residue was washed with the minimum amount of Et$_2$O and the resultant precipitate filtered to obtain the title compound as a white solid (81%); MS (ES$^+$) m/z 521 (M+H)$^+$.

Step 5: 3-[2-(2-aminophenyl)-3-cyclohexyl-6-(methoxycarbonyl)-1H-indol-1-yl]propanoic Acid To a solution of 3-[2-{2-[(tert-butoxycarbonyl)amino]phenyl}-3-cyclohexyl-6-(methoxycarbonyl)-1H-indol-1-yl]propanoic acid in DCM (0.05 M) a large excess (>100 eq) of TFA was added and the solution was stirred at RT for 1 h. The volatiles were removed in vacuo to afford the title compound (quant); MS (ES$^+$) m/z 421 (M+H)$^+$.

Step 6: methyl 14-cyclohexyl-6-oxo-5,6,7,8-tetrahydroindolo[1,2e][1,5]benzodiazocine-11-carboxylate To a solution of 3-[2-(2-aminophenyl)-3-cyclohexyl-6-(methoxycarbonyl)-1H-indol-1-yl]propanoic acid in DCM (0.01 M), 3.5 eq of DIPEA and 1.2 eq of HATU were added and the mixture was stirred at RT for 15 mins. DCM was removed in vacuo, the residue was taken up in acetone and 1N HCl was added until pH=2. The resulting precipitate was filtered and dried to give the product in 75% yield; MS (ES$^+$) m/z 403 (M+H)$^+$.

Step 7: methyl 14-cyclohexyl-5-[2-(dimethylamino)ethyl]-6-oxo-5,6,7,8-tetrahydroindolo[1,2-e][1,5]benzodiazocine-11-carboxylate NaH (1.4 eq, 60% dispersion in mineral oil) was added to a solution of methyl 14-cyclohexyl-6-oxo-5,6,7,8-tetrahydroindolo[1,2-e][1,5]benzodiazocine-11-carboxylate in DMF (0.1 M) and the solution allowed to stir at RT for 1 h. In the meantime, a 1:1 equimolar mixture of (2-chloroethyl)dimethylamine hydrochloride and NaH (60% dispersion in mineral oil) in solution in DMF (0.5 M) was prepared. After 30 mins, this mixture (2.5 eq of (2-chloroethyl)dimethylamine) was slowly added to the solution of indole anion and the mixture was stirred at RT overnight. DMF was removed in vacuo and the residue taken up in EtOAc. The organic phase was washed with H$_2$O (twice) and then brine before being dried over Na$_2$SO$_4$, filtered and the solvent evaporated in vacuo. The crude compound was used in the next step without further purification; MS (ES$^+$) m/z 474 (M+H)$^+$.

Step 8: 14-cyclohexyl-5-[2-(dimethylamino)ethyl]-6-oxo-5,6,7,8-tetrahydroindolo[1,2-e][1,5]benzodiazocine-11-carboxylic Acid To a solution of methyl 14-cyclohexyl-5-[2-(dimethylamino)ethyl]-6-oxo-5,6,7,8-tetrahydroindolo[1,2-e][1,5]benzodiazocine-11-carboxylate in DCM (0.1M) 7 eq BBr$_3$ (1M solution in DCM) were added. The solution stirred at RT for 20 mins. The volatiles were evaporated in vacuo. The crude was then purified by prep RP-HPLC (stationary phase: column Waters XTERRA prep. C18, 5 um, 19×150 mm. Mobile phase: MeCN/H$_2$O buffered with 0.1% TFA). Fractions containing the pure compound were combined and freeze dried to afford the title compound (40% over two steps).

$^1$H NMR (400 MHz, DMSO-d$_6$, 300 K) δ 1.10-1.35 (m, 3H), 1.50-1.60 (m, 1H), 1.60-1.75 (m, 2H), 1.80-2.00 (m, 4H), 2.40-2.45 (m, 1H partially obscured by DMSO peak), 2.70 (s, 6H), 2.72-2.80 (m, 2H), 2.90-3.15 (m, 2H), 3.20-3.40 (m, 1H obscured by H$_2$O peak), 3.61-3.75 (m, 1H), 3.80-3.90 (m, 1H), 4.75-4.85 (m, 1H), 7.53-7.58 (m, 1H), 7.60-7.68 (m, 3H), 7.69-7.75 (m, 1H), 7.86 (d, J 8.4, 1H), 8.14 (s, 1H), 9.27 (br s, 1H); MS (ES$^+$) m/z 460 (M+H)$^+$.

EXAMPLE 9

14-cyclohexyl-5-[2-(dimethylamino)ethyl]-5,6,7,8-tetrahydroindolo[1,2-e][1,5]benzodiazocine-11-carboxylic Acid To a solution of methyl 14-cyclohexyl-5-[2-(dimethylamino)ethyl]-6-oxo-5,6,7,8-tetrahydroindolo[1,2-e][1,5]benzodiazocine-11-carboxylate (prepared as described in Example 8, Step 7) in THF (0.1 M), BH$_3$.Me$_2$S (20 eq, 2 M solution in THF) was added. The solution was stirred overnight at RT. MeOH was carefully added to the mixture to quench the reaction, followed by an excess of 1 N NaOH (>10 eq). The mixture was heated at 60° C. for 12 h. The solvent was evaporated in vacuo. The crude was then purified by prep RP-HPLC (stationary phase: column Waters XTERRA prep. C18, 5 um, 19×100 mm. Mobile phase: MeCN/H$_2$O buffered with 0.1% TFA). Fractions containing the pure compound were combined and freeze dried to afford the title compound (24% over three steps).

$^1$H NMR (300 MHz, DMSO-d$_6$+TFA, 300 K) δ 1.15-1.40 (m, 3H), 1.50-1.58 (m, 1H), 1.60-1.75 (m, 3H), 1.80-2.00 (m, 5H), 2.55-2.65 (m, 1H), 2.74 (s, 3H), 2.78 (s, 3H), 2.90-3.10 (m, 2H), 3.10-3.30 (m, 4H), 3.55-3.65 (m, 1H), 4.50-4.65 (m, 1H), 6.95-7.01 (m, 1H), 7.10-7.20 (m, 2H), 7.35-7.45 (m, 1H), 7.64 (d, J 8.2, 1H), 7.84 (d, J 8.2, 1H), 8.09 (s, 1H); MS (ES$^+$) m/z 446 (M+H)$^+$.

EXAMPLE 10

14-cyclohexyl-5-methyl-5,6,7,8-tetrahydroindolo[1,2-e][1,5]benzodiazocine-11-carboxylic Acid Step 1: methyl 14-cyclohexyl-5,6,7,8-tetrahydroindolo[1,2-e 1,5]benzodiazocine-11-carboxylate To a solution of methyl 14-cyclohexyl-6-oxo-5,6,7,8-tetrahydroindolo[1,2-e][1,5]benzodiazocine-11-carboxylate (prepared as described in Example 8, Step 6) in THF (0.15 M), 20 eq of BH$_3$.Me$_2$S (2 M sol. in THF) were added and the mixture was stirred at RT for 6 h. The solution was carefully quenched by adding MeOH until effervescence subsided. The volatiles were then evaporated in vacuo. The crude residue was used directly in the next step; MS (ES$^+$) m/z 389 (M+H)$^+$.

Step 2: methyl 14-cyclohexyl-5-methyl-5,6,7,8-tetrahydroindolo[1,2-e ][1,5]benzodiazocine-11-carboxylate To a solution of methyl 14-cyclohexyl-5,6,7,8-tetrahydroindolo[1,2-e][1,5]benzodiazocine-11-carboxylate in DCE (0.05 M) 1 eq of formaldehyde (37 wt. % sol. in H$_2$O) and 2 eq of NaBH(OAc)$_3$ were added and the solution stirred at RT for 1 h. The reaction mixture was diluted with EtOAc. The organic phase was washed with NaHCO$_3$ (s.s.) and brine. The organic phase was dried over Na$_2$SO$_4$ filtered and concentrated in vacuo. The title compound was used directly in the next step; MS (ES$^+$) m/z 403 (M+H)$^+$.

Step 3: 14-cyclohexyl-5-methyl-5,6,7,8-tetrahydroindolo[1,2-e][1,5]benzodiazocine-11-carboxylic Acid To a solution of methyl 14-cyclohexyl-5-methyl-5,6,7,8-tetrahydroindolo[1,2-e][1,5]benzodiazocine-11-carboxylate in DCM (0.1 M), 5 eq of BBr$_3$ (1 M sol. in DCM) were added. The solution was stirred at RT for 20 mins. The solvent was evaporated in vacuo. The crude was then purified by automated prep RP-HPLC (stationary phase: column Waters XTERRA prep. C18, 5 um, 19×100 mm. Mobile phase: MeCN/H$_2$O buffered with 0.1% TFA). Fractions containing the pure compound were combined and freeze dried to afford the title compound (60% over two steps).

$^1$H NMR (400 MHz, DMSO-d$_6$+TFA, 300 K) δ 1.10-1.60 (m, 5H), 1.60-1.80 (m, 2H), 1.80-2.10 (m, 5H), 2.65-2.75 (m, 2H), 2.85-2.95 (m, 1H), 2.98 (s, 3H), 3.55-3.68 (m, 1H), 4.55-4.65 (m, 1H), 6.65-6.75 (m, 1H), 6.84 (d, J 8.4, 1H), 7.03 (d, J 7.6, 1H), 7.27-7.32 (m, 1H), 7.63 (d, J 8.4, 1H), 7.81 (d, J 8.4, 1H), 8.08 (s, 1H), MS (ES$^+$) m/z 389 (M+H)$^+$.

EXAMPLE 11

14-cyclohexyl-7-(dimethylamino)-5-methyl-5,6,7,8-tetrahydroindolo[1,2-e][1,5]benzodiazocine-11-carboxylic Acid Step 1: methyl 2-[bis(tert-butoxycarbonyl)amino]acrylate To a solution of methyl N-(tert-butoxycarbonyl)serinate in MeCN (0.9 M) were added 2.5 eq of di-tert-butyl dicarbonate and 0.1 eq of DMAP. The solution was stirred at RT for 48 h, before being quenched with saturated aqueous NaHCO$_3$ and extracted (twice) with EtOAc. The combined organics were washed with saturated aqueous NH$_4$Cl and brine before being dried over Na$_2$SO$_4$, filtered and concentrated in vacuo to give the title compound as a cream solid (quantitative); MS (ES$^+$) m/z 324 (M+Na)+.

Step 2: methyl 1-{2-[bis(tert-butoxycarbonyl)amino]-3-methoxy-3-oxopropyl}-2-bromo-3-cyclohexyl-1H-indole-6-carboxylate To a solution of methyl 2-bromo-3-cyclohexyl-1H-indole-6-carboxylate (prepared as described in WO 2004087714 from commercially available methyl indole-6-carboxylate) in MeCN (0.08 M) were added 6 eq of K$_2$CO$_3$ and 1.2 eq of methyl 2-[bis(tert-butoxycarbonyl)amino]acrylate. The mixture was stirred at RT for 16 h before being filtered and concentrated in vacuo to afford the title compound as a viscous oil which solidified on standing (quantitative); MS (ES$^+$) m/z 659 (M+Na)$^+$, 661 (M+Na)$^+$.

Step 3: methyl 2-bromo-1-2-[(tert-butoxycarbonyl)amino]-3-methoxy-3-oxopropyl)-3-cyclohexyl-1H-indole-6-carboxylate To a solution of methyl 1-(2-[bis(tert-butoxycarbonyl)amino]-3-methoxy-3-oxopropyl)-2-bromo-3-cyclohexyl-1H-indole-6-carboxylate in CH$_2$Cl$_2$ (0.15 M), were added 2 eq of TFA. The solution was stirred at RT for 10 mins before being concentrated in vacuo. RP-HPLC analysis of the reaction mixture showed about 50% deprotection of the Boc amine. The residue was redissolved in CH$_2$Cl$_2$ and a further 2 eq of TFA added. After stirring for 10 mins at RT, the volatiles were again removed in vacuo. This time RP-HPLC showed that complete mono-deprotection of the amine had occurred (quantitative); MS (ES$^+$) m/z 559 (M+Na)$^+$, 561 (M+Na)$^+$.

Step 4: 3-[2-(2-aminophenyl)-3-cyclohexyl-6-(methoxycarbonyl)-1H-indol-1-yl]-N-(tert-butoxycarbonyl)alanine To a solution of methyl 2-bromo-1-{2-[(tert-butoxycarbonyl)amino]-3-methoxy-3-oxopropyl}-3-cyclohexyl1H-indole-6-carboxylate in nBuOH:H$_2$O (9:1, 0.08 M) were added 1.5 eq of 2-(4,4,5,5-tetramethyl-1,3,2-dioxaborolan-2-yl)aniline, 6 eq of K$_3$PO$_4$, 5 mol % of dicyclohexyl(2',6'-dimethoxybiphenyl-2-yl)phosphine and 2.5 mol % of palladium acetate. The mixture was heated at 90° C. for 4 h. After cooling to RT, the mixture was acidified with HCl (1N) and extracted (twice) with EtOAc. The combined organics were washed with brine and dried over Na$_2$SO$_4$ before being filtered and concentrated in vacuo. The crude product mixture was redissolved in THF:H$_2$O (1:1, 0.08 M) and 2 eq LiOH added. After stirring for 1 h, ester deprotection was complete as evidenced by RP-HPLC analysis. The volatiles were removed in vacuo and the residue partitioned between EtOAc and H$_2$O. The organics were washed with brine and dried over Na$_2$SO$_4$ before being filtered and concentrated in vacuo. The crude residue was used directly in the next step; MS (ES$^+$) m/z 536 (M+H)$^+$, 558 (M+Na)$^+$.

Step 5: methyl 7-[(tert-butoxycarbonyl)amino]1-14-cyclohexyl-6-oxo-5,6,7,8-tetrahydroindolo[1,2-e][1,5]benzodiazocine-11-carboxylate To a solution of 3-[2-(2-aminophenyl)-3-cyclohexyl-6-(methoxycarbonyl)-1H-indol-1-yl]-N-(tert-butoxycarbonyl)alanine in CH$_2$Cl$_2$ (0.02 M) were added 3 eq of iPr$_2$NEt and 1.2 eq of HATU and the mixture stirred at RT for 16 h. The reaction was quenched with saturated aqueous NaHCO$_3$ and extracted (twice) with EtOAc. The combined organics were washed with HCl (1N) and brine before being dried over Na$_2$SO$_4$, filtered and concentrated in vacuo. The crude was purified by flash chromatography (5-20% EtOAc/1% Et$_3$N/PE) to afford the title compound as an oil in 12% yield (3 steps); MS (ES$^+$) m/z 518 (M+H)$^+$, 540 (M+Na)$^+$.

Step 6: methyl 7-[(tert-butoxycarbonyl)amino 1-14-cyclohexyl-5,6,7,8-tetrahydroindolo [1.2-e]1,5]benzodiazocine-11-carboxylate To a solution of methyl 7-[(tert-butoxycarbonyl)amino]-14-cyclohexyl-6-oxo-5,6,7,8-tetrahydroindolo [1,2-e][1,5]benzodiazocine-11-carboxylate in THF (0.02 M), 10 eq of BH$_3$.THF (2 M solution in THF) were added and the mixture was stirred at RT for 4 h. All volatiles were removed under reduced pressure and the crude residue was used directly in the next step; MS (ES$^+$) m/z 504 (M+H)$^+$, 526 (M+Na)$^+$.

Step 7: methyl 7-amino-14-cyclohexyl-5,6,7,8-tetrahydroindolo[2,2-][1,5]benzodiazocine-11-carboxylate To a solution of methyl 7-[(tert-butoxycarbonyl)amino]-14-cyclohexyl-5,6,7,8-tetrahydroindolo [1,2e][1,5]benzodiazocine-11-carboxylate in CH$_2$Cl$_2$ (0.02 M), was added 100 eq of TFA. The solution was stirred at RT for 45 mins before being concentrated in vacuo to afford the product as a viscous oil (quantitative); MS (ES$^+$) m/z 404 (M+H)$^+$ Step 8: methyl 14-cyclohexyl-7-(dimethylamino)-5-methyl-5,6,7,8-tetrahydroindolo[1.2-e][1,5]benzodiazocine-11-carboxylate To a solution of methyl 7-amino-14-cyclohexyl-5,6,7,8-tetrahydroindolo[1,2-e][1,5]benzodiazocine-11-carboxylate in CH$_2$Cl$_2$ (0.02 M) were added 5 eq of formaldehyde (37% in H$_2$O) and the pH adjusted to pH 4 with trimethylamine. The solution was stirred at RT for 30 mins before addition of 3 eq of NaBH$_3$CN and the mixture stirred at RT for 16 h. The reaction was quenched with saturated aqueous NaHCO$_3$ and extracted (twice) with EtOAc. The combined organics were washed with brine before being dried over Na$_2$SO$_4$, filtered and concentrated in vacuo to give the title compound as a viscous-oil (quantitative); MS (ES$^+$) r/z 446 (M+H)$^+$.

Step 9: 14-cyclohexyl-7-(dimethylamino)-5-methyl-5,6,7,8-tetrahydroindolo[1,2-e][1,5]benzodiazocine-11-carboxylic Acid To a solution of methyl 14-cyclohexyl-7-(dimethylamino)-5-methyl-5,6,7,8-tetrahydroindolo[1,2-e][1,5]benzodiazocine-11-carboxylate in MeOH (0.05 M), 40 eq 2N NaOH were added and the reaction stirred at 65° C. for 3 h. The reaction was acidified to pH 2 with HCl and the solvent was evaporated in vacuo. The crude was then purified by prep RP-HPLC (stationary phase: column Waters XTERRA prep. C18, 5 um, 19×150 mm. Mobile phase: acetonitrile/H$_2$O buffered with 0.1% TFA). Fractions containing the pure compound were combined and freeze dried to afford the title compound as a brown powder in 8 % yield (over four steps).

$^1$H NMR (400 MHz, DMSO-d$_6$ +TFA, 300 K) δ 1.15-1.34 (m, 3H), 1.54-1.94 (m, 7H), 2.62-2.68 (m, 1H), 2.86 (s, 3H), 2.96 (s, 6H), 3.13-3.17 (m, 1H), 3.36-3.41 (m, 1H), 3.59-3.62 (m, 1H), 3.88-3.94 (m, 1H), 4.93-4.98 (m, 1H), 7.00-7.03 (m, 1H), 7.13-7.15 (m, 2H), 7.42-7.46 (m, 1H), 7.72 (d, J8.3, 1H), 7.86 (d, J 8.3, 1H), 8.29 (s, 1H); MS (ES$^+$) m/z 432 (M+H)$^+$.

The following table contains further examples:

TABLE 1

| Example no. | Name | m/z (ES$^+$) |
|---|---|---|
| 101 | 13-cyclohexyl-5-[2-(dimethylamino)ethoxy]-6,7-dihydro-5H-indolo[2,1-a][2]benzazepine-10-carboxylic acid | 447 |
| 102 | 13-cyclohexyl-5-[2-(diethylamino)ethoxy]-6,7-dihydro-5H-indolo[2,1-a][2]benzazepine-10-carboxylic acid | 475 |
| 103 | 13-cyclohexyl-6-[2-(diethylamino)ethoxy]-6,7-dihydro-5H-indolo[2,1-a][2]benzazepine-10-carboxylic acid | 475 |
| 104 | 13-cyclohexyl-3-methoxy-6-(2-pyrrolidin-1-ylethoxy)-6,7-dihydro-5H-indolo[2,1-a][2]benzazepine-10-carboxylic acid | 503 |
| 105 | 13-cyclohexyl-3-methoxy-5-(2-pyrrolidin-1-ylethoxy)-6,7-dihydro-5H-indolo[2,1-a][2]benzazepine-10-carboxylic acid | 503 |

The invention claimed is:

1. A compound of formula (Ib) or a pharmaceutically acceptable salt thereof:

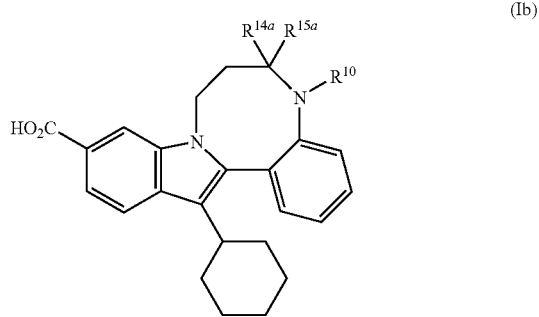

(Ib)

wherein $R^{10}$ is hydrogen, $C_{1-6}$alkyl, $C_{2-6}$alkyl, $C_{2-6}$alkenyl or $(CH_2)_{1-3}NR^{16}R^{17}$;

$R^{16}$ and $R^{17}$ are independently selected from hydrogen and $C_{1-6}$alkyl;

$R^{14a}$ and $R^{15a}$ are independently selected from hydrogen, $C_{1-6}$alkyl or $C_{2-6}$alkenyl.

2. The compound as claimed in claim 1, wherein $R^{10}$ is hydrogen, $C_{1-6}$alkyl or $(CH_2)_{1-3}NR^{16}R^{17}$.

3. The compound as claimed in claim 1, wherein $R^{14a}$ and $R^{15a}$ are independently selected from hydrogen or $C_{1-6}$alkyl.

4. A compound of formula (Ic) or a pharmaceutically acceptable salt thereof:

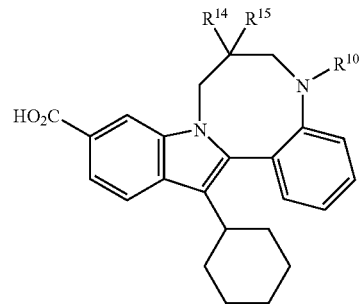

(Ic)

wherein $R^{10}$ is hydrogen, $C_{1-6}$alkyl or $C_{2-6}$alkenyl;

$R^{14}$ and $R^{15}$ are independently selected from hydrogen, $C_{1-6}$alkyl, $C_{2-6}$alkenyl or $(CH_2)_{0-3}NR^{16}R^{17}$; and $R^{16}$ and $R^{17}$ are independently selected from hydrogen and $C_{1-6}$alkyl.

5. The compound as claimed in claim 4, wherein $R^{10}$ is hydrogen or $C_{1-6}$alkyl.

6. The compound as claimed in claim 4, wherein $R^{14}$ and $R^{15}$ are independently selected from hydrogen, $C_{1-6}$alkyl or $(CH_2)_{0-3}NR^{16}R^{17}$, where $R^{16}$ and $R^{17}$ are independently selected from hydrogen and $C_{1-4}$alkyl.

7. A compound selected from the group consisting of:
14-cyclohexyl-5-[2-(dimethylamino)ethyl]-5,6,7,8-tetrahydroindolo [1,2-e][1,5]benzodiazocine-11-carboxylic acid,
14-cyclohexyl-5-methyl-5,6,7,8-tetrahydroindolo[1,2-e][1,5]benzodiazocine-11-carboxylic acid, and
14-cyclohexyl-7-(dimethylamino)-5-methyl-5,6,7,8-tetrahydroindolo[1,2-e][1,5]benzodiazocine-11-carboxylic acid,
and pharmaceutically acceptable salts thereof.

8. A pharmaceutical composition comprising a compound as claimed in claim 1, in association with a pharmaceutically acceptable carrier.

9. The pharmaceutical composition as claimed in claim 8, which further comprises one or more other agents for the treatment of viral infections, or an immunomodulatory agent.

10. A method of preparation of a pharmaceutical composition, involving admixing at least one compound as claimed in claim 1, with one or more pharmaceutically acceptable adjuvants, diluents or carriers and/or with one or more other therapeutically or prophylactically active agents.

* * * * *